(12) United States Patent
Raslambekov

(10) Patent No.: US 11,678,959 B2
(45) Date of Patent: *Jun. 20, 2023

(54) SYSTEMS AND METHODS FOR DETERMINING A TOOTH TRAJECTORY

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 229 days.

This patent is subject to a terminal disclaimer.

(21) Appl. No.: 17/245,463

(22) Filed: Apr. 30, 2021

(65) Prior Publication Data

US 2022/0071740 A1 Mar. 10, 2022

Related U.S. Application Data

(63) Continuation of application No. 17/014,107, filed on Sep. 8, 2020, now Pat. No. 10,993,782.

(51) Int. Cl.
*G06K 9/00* (2022.01)
*A61C 3/00* (2006.01)
(Continued)

(52) U.S. Cl.
CPC ............... *A61C 7/08* (2013.01); *A61B 5/1111* (2013.01); *A61C 7/002* (2013.01); *A61C 9/004* (2013.01);
(Continued)

(58) Field of Classification Search
CPC .................................... G06K 9/00; A61C 3/00
(Continued)

(56) References Cited

U.S. PATENT DOCUMENTS 5,975,893 A 11/1999 Chishti et al.
6,183,248 B1 2/2001 Chishti et al.
(Continued)

FOREIGN PATENT DOCUMENTS

CN 102415916 A 4/2012
EP 1119309 B1 6/2016
(Continued)

OTHER PUBLICATIONS

Wu, "A biomechanical case study on the optimal orthodontic force on the maxillary canine tooth based on finite element analysis", Jul. 19, 2018, Journal of Zhejiang University Science B 19(7):535-546; DOI: 10.1631/jzus.B1700195.
(Continued)

*Primary Examiner* — Seyed H Azarian
(74) *Attorney, Agent, or Firm* — BCF LLP

(57) ABSTRACT

A method and a system for determining a tooth trajectory for a given tooth of a subject are provided. The method comprises: generating, by executing an optimization algorithm, based on a 3D model of the given tooth, a plurality of segments defining a tooth trajectory of the given tooth from its initial position to its target position. The executing comprises: determining, based on the stress values range, an initial force to be applied to the given tooth, the initial force causing a maximum displacement of the 3D model of the given tooth from the start position associated with the given segment towards the target position associated with the given tooth, thereby identifying an end position associated with the given segment. The method further comprises determining a respective force applied to at least one other 3D model by the maximum displacement of the 3D model of the given tooth.

17 Claims, 11 Drawing Sheets

(51) Int. Cl.
*A61C 7/08* (2006.01)
*A61B 5/11* (2006.01)
*A61C 13/34* (2006.01)
*A61C 9/00* (2006.01)
*A61C 7/00* (2006.01)
*G06T 19/00* (2011.01)
*G06T 7/10* (2017.01)
*G06T 7/00* (2017.01)
*G06T 7/60* (2017.01)
*G06T 17/10* (2006.01)

(52) U.S. Cl.
CPC ............ *A61C 13/34* (2013.01); *G06T 7/0012* (2013.01); *G06T 7/10* (2017.01); *G06T 7/60* (2013.01); *G06T 17/10* (2013.01); *G06T 19/00* (2013.01); *G06T 2210/21* (2013.01); *G06T 2210/41* (2013.01)

(58) Field of Classification Search
USPC ....... 382/100, 103, 106, 128–131, 154, 162, 382/168, 173, 181, 199, 209, 224, 254, 382/220, 285–294, 305, 312; 433/16, 24, 433/18, 213
See application file for complete search history.

(56) References Cited

U.S. PATENT DOCUMENTS

| | | |
|---|---|---|
| 6,227,850 B1 | 5/2001 | Chishti et al. |
| 6,309,215 B1 | 10/2001 | Phan et al. |
| 6,318,994 B1 | 11/2001 | Chishti et al. |
| 6,334,853 B1 | 1/2002 | Kopelman et al. |
| 6,386,878 B1 | 5/2002 | Pavloskaia et al. |
| 6,398,548 B1 | 6/2002 | Muhammad et al. |
| 6,463,344 B1 | 10/2002 | Pavloskaia et al. |
| 6,471,511 B1 | 10/2002 | Chishti et al. |
| 6,554,611 B2 | 4/2003 | Chishti et al. |
| 6,602,070 B2 | 8/2003 | Miller et al. |
| 6,632,089 B2 | 10/2003 | Rubbert et al. |
| 6,665,570 B2 | 12/2003 | Pavloskaia et al. |
| 6,685,470 B2 | 2/2004 | Chishti et al. |
| 6,688,886 B2 | 2/2004 | Hughes et al. |
| 6,705,863 B2 | 3/2004 | Phan et al. |
| 6,726,478 B1 | 4/2004 | Isiderio et al. |
| 6,739,870 B2 | 5/2004 | Lai et al. |
| 6,767,208 B2 | 7/2004 | Kaza |
| 6,979,196 B2 | 12/2005 | Nikolskiy et al. |
| 7,040,896 B2 | 5/2006 | Pavlovskaia et al. |
| 7,059,850 B1 | 6/2006 | Phan et al. |
| 7,063,532 B1 | 6/2006 | Jones et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,220,122 B2 | 5/2007 | Chishti |
| 7,241,142 B2 | 7/2007 | Abolfathi et al. |
| 7,293,988 B2 | 11/2007 | Wen |
| 7,320,592 B2 | 1/2008 | Chishti et al. |
| 7,373,286 B2 | 5/2008 | Nikolskiy et al. |
| 7,377,778 B2 | 5/2008 | Chishti et al. |
| 7,428,481 B2 | 9/2008 | Nikolskiy et al. |
| 7,442,040 B2 | 10/2008 | Kuo |
| 7,637,740 B2 | 12/2009 | Knopp |
| 7,689,398 B2 | 3/2010 | Cheng et al. |
| 7,771,195 B2 | 8/2010 | Knopp et al. |
| 7,826,646 B2 | 11/2010 | Pavlovskaia et al. |
| 7,841,858 B2 | 11/2010 | Knopp et al. |
| 7,844,429 B2 | 11/2010 | Matov et al. |
| 7,865,259 B2 | 1/2011 | Kuo et al. |
| 7,904,307 B2 | 3/2011 | Abolfathi et al. |
| 7,905,725 B2 | 3/2011 | Chishti et al. |
| 7,942,672 B2 | 5/2011 | Kuo |
| 7,993,134 B2 | 8/2011 | Wen |
| 8,038,444 B2 | 10/2011 | Kitching et al. |
| 8,044,954 B2 | 10/2011 | Kitching et al. |
| 8,057,226 B2 * | 11/2011 | Wiechmann ............ A61C 7/20 433/18 |
| 8,108,189 B2 | 1/2012 | Chelnokov et al. |
| 8,131,393 B2 | 3/2012 | Matov et al. |
| 8,135,569 B2 | 3/2012 | Matov et al. |
| 8,244,390 B2 | 8/2012 | Kuo et al. |
| 8,439,672 B2 | 5/2013 | Matov et al. |
| 8,465,280 B2 | 6/2013 | Sachdeva et al. |
| 8,478,435 B2 | 7/2013 | Kuo et al. |
| 8,639,477 B2 | 1/2014 | Chelnokov et al. |
| 8,641,414 B2 | 2/2014 | Borovinskih et al. |
| 8,734,150 B2 | 5/2014 | Wen |
| 8,780,106 B2 | 7/2014 | Chishti et al. |
| 8,807,999 B2 | 8/2014 | Kuo et al. |
| 8,896,592 B2 | 11/2014 | Boltunov et al. |
| 8,897,902 B2 | 11/2014 | See et al. |
| 8,961,173 B2 | 2/2015 | Miller |
| 9,060,829 B2 | 6/2015 | Sterental et al. |
| 9,107,722 B2 | 8/2015 | Matov et al. |
| 9,161,823 B2 | 10/2015 | Morton et al. |
| 9,211,166 B2 | 12/2015 | Kuo et al. |
| 9,326,831 B2 | 5/2016 | Cheang |
| 9,345,557 B2 | 5/2016 | Anderson et al. |
| 9,375,293 B2 | 6/2016 | Taub et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,433,478 B2 | 9/2016 | Wucher |
| 9,529,970 B2 | 12/2016 | Andreiko |
| 9,592,103 B2 | 3/2017 | Taub et al. |
| 9,610,140 B2 | 4/2017 | Anderson et al. |
| 9,622,834 B2 | 4/2017 | Chapoulaud et al. |
| 9,792,413 B2 | 10/2017 | Badawi |
| 9,844,424 B2 | 12/2017 | Wu et al. |
| 10,011,050 B2 | 7/2018 | Kitching et al. |
| 10,076,389 B2 | 9/2018 | Wu et al. |
| 10,278,794 B1 * | 5/2019 | Raslambekov ........ B33Y 50/02 |
| 10,307,222 B2 | 6/2019 | Morton et al. |
| 10,332,164 B2 | 6/2019 | Abolfathi et al. |
| 10,383,704 B2 | 8/2019 | Kitching |
| 10,405,947 B1 | 9/2019 | Kaza et al. |
| 10,405,951 B1 | 9/2019 | Kopelman et al. |
| 10,413,385 B2 | 9/2019 | Sherwood et al. |
| 10,426,574 B2 | 10/2019 | Raby et al. |
| 10,433,934 B2 | 10/2019 | Kopelman |
| 10,463,452 B2 | 11/2019 | Matov et al. |
| 10,470,846 B2 | 11/2019 | Kopelman et al. |
| 10,524,880 B2 | 1/2020 | Wen |
| 10,553,309 B2 | 2/2020 | Trosien et al. |
| 10,561,476 B2 | 2/2020 | Matov et al. |
| 10,595,965 B2 | 3/2020 | Khardekar et al. |
| 10,617,489 B2 | 4/2020 | Grove et al. |
| 10,650,517 B2 | 5/2020 | Parpara et al. |
| 10,653,503 B2 | 5/2020 | Boltunov et al. |
| 10,695,146 B1 | 6/2020 | Raslambekov et al. |
| 10,695,147 B1 | 6/2020 | Raslambekov |
| 10,783,629 B2 | 9/2020 | Parpara et al. |
| 10,792,127 B2 | 10/2020 | Kopelman et al. |
| 10,813,721 B2 | 10/2020 | Sterental et al. |
| 2005/0208453 A1 * | 9/2005 | Abolfathi ................. A61C 7/00 433/213 |
| 2005/0244791 A1 | 11/2005 | Davis et al. |
| 2013/0095446 A1 | 4/2013 | Andreiko et al. |
| 2014/0288894 A1 | 9/2014 | Chishti et al. |
| 2016/0302885 A1 | 10/2016 | Matov et al. |
| 2017/0035536 A1 | 2/2017 | Alvarez Garcia et al. |
| 2017/0079748 A1 | 3/2017 | Andreiko |
| 2017/0100213 A1 * | 4/2017 | Kuo ...................... G16H 20/40 |
| 2018/0039755 A1 | 2/2018 | Matov et al. |
| 2018/0165818 A1 | 6/2018 | Tsai et al. |
| 2018/0304497 A1 | 10/2018 | Kitching et al. |
| 2019/0000592 A1 | 1/2019 | Cam et al. |
| 2019/0046295 A1 | 2/2019 | Morton et al. |
| 2019/0046298 A1 * | 2/2019 | Cinader, Jr. ............ A61C 7/14 |
| 2019/0282333 A1 | 9/2019 | Matov et al. |
| 2019/0314117 A1 | 10/2019 | Morton et al. |
| 2019/0357997 A1 | 11/2019 | Shi et al. |
| 2020/0000551 A1 | 1/2020 | Li et al. |
| 2020/0000552 A1 | 1/2020 | Mednikov et al. |

(56) References Cited

U.S. PATENT DOCUMENTS

| | | | |
|---|---|---|---|
| 2020/0146775 A1 | 5/2020 | Wen et al. | |
| 2020/0146776 A1 | 5/2020 | Matov et al. | |
| 2020/0229900 A1 | 7/2020 | Cunliffe et al. | |
| 2020/0297459 A1 | 9/2020 | Grove et al. | |
| 2020/0306012 A1 | 10/2020 | Roschin et al. | |
| 2020/0345455 A1* | 11/2020 | Roein Peikar | A61C 7/146 |

FOREIGN PATENT DOCUMENTS

| | | |
|---|---|---|
| WO | 98058596 A1 | 12/1998 |
| WO | 00019928 A1 | 4/2000 |
| WO | 00019930 A1 | 4/2000 |
| WO | 00019931 A1 | 4/2000 |
| WO | 00069356 A1 | 11/2000 |
| WO | 00069357 A1 | 11/2000 |
| WO | 01074268 A1 | 11/2001 |
| WO | 2018085718 A2 | 5/2018 |
| WO | 2019089989 A2 | 5/2019 |

OTHER PUBLICATIONS

Optimum force magnitude for orthodontic u tooth movement: A mathematic model Yijin Ren, DDS, PhD,a Jaap C. Maltha, PhD,b Martin A. Van 't Hof, PhD,c and Anne Marie Kuijpers-Jagtman, (Feb. 2003).

* cited by examiner

SYSTEMS AND METHODS FOR DETERMINING A TOOTH TRAJECTORY

CROSS-REFERENCE

The present application is a continuation of U.S. patent application Ser. No. 17/014,107 filed on Sep. 8, 2020 and entitled "SYSTEMS AND METHODS FOR DETERMINING A TOOTH TRAJECTORY", the content of which is incorporated herein by reference in its entirety.

FIELD

The present technology relates to systems and methods for planning an orthodontic treatment for a patient, in general; and more specifically, to determining a tooth trajectory for a patient's tooth.

BACKGROUND

In orthodontics, planning an orthodontic treatment for a subject may include determining a tooth trajectory for each tooth of a subject's arch form. This may further include modelling tooth movements of a given tooth in the course of the planned orthodontic treatment: from an initial (current) position to a target position of the given tooth, the target position being typically associated with alignment of the given tooth within the subject's arch form.

Further, once the tooth movements have been modelled, an orthodontic device, such as an aligner (or a set thereof), may be produced and applied to the subject's arch form to exert an external force, over a predetermined treatment interval, onto the given tooth causing it to move, along the so determined tooth trajectory, towards the target position.

However, there are certain contrasting requirements related to the orthodontic treatment: (1) efficiency requirement—minimizing an overall duration of the orthodontic treatment, and (2) safety requirement—ensuring that the planned orthodontic treatment does not cause damage to the subject's teeth or other buccal anatomical structures through collisions or excess applied forces.

Certain prior art approaches have been proposed to address the technical problem of generating the tooth trajectory for the given tooth considering the above-identified requirements.

U.S. Pat. No. 7,241,142-B2 issued on Jul. 10, 2007, assigned to Align Technology Inc., and entitled "Root-Based Tooth Moving Sequencing" discloses systems and methods for repositioning the teeth of a patient by providing a digital model of each tooth of the patient; determining one or more root parameters from the digital model; and digitally moving one or more tooth models and evaluating a treatment outcome based on one or more root movement clinical constraints.

U.S. Pat. No. 8,038,444-B2 issued on Oct. 18, 2011, assigned to Align Technology Inc., and entitled "Automated Treatment Staging for Teeth" discloses an apparatus, a system, and methods for utilizing one or more computing devices to stage the movement of teeth during an alignment treatment. The computing device receives an electronic representation of the patient's teeth in their initial position and an electronic representation of the teeth in a final position for each tooth. A route each tooth will travel to reach its final position is determined, and the teeth are scheduled to move according to a movement pattern. Moreover, the schedule of movement takes into account a maximum rate of tooth movement for each tooth, the path of movement for each tooth, the distance each tooth needs to move, any needed tooth staggering, any needed round-tripping or tooth movement slowing. The invention also includes techniques for determining an optimum number of stages for the treatment based on the schedule of movement.

European Patent No.: 1,119,309-B1 issued on Jun. 1, 2016, assigned to Align Technology Inc., and entitled "Computer Automated Development of an Orthodontic Treatment Plan and Appliance" discloses a computer used to create a plan for repositioning an orthodontic patient's teeth. The computer receives an initial digital data set representing the patient's teeth at their initial positions and a final digital data set representing the teeth at their final positions. The computer then uses the data sets to generate treatment paths along which teeth will move from the initial positions to the final positions.

An article "*A Biomechanical Case Study on the Optimal Orthodontic Force on the Maxillary Canine Tooth Based on Finite Element Analysis*" written by Jian-lei Wu. Yun-feng Liu, Wei Peng, Hui-yue Dong, and Jian-xing Zhang, and published in Journal of Zhejiang University-SCIENCE B (Biomedicine & Biotechnology) discloses developing finite element models of a maxillary canine and surrounding tissues for investigating the optimal orthodontic forces on a maxillary canine, using hydrostatic stress and logarithmic strain of the periodontal ligament (PDL) as indicators.

SUMMARY

It is an object of the present technology to ameliorate at least some of the inconveniences present in the prior art.

The developers of the present technology have devised a method for generating the tooth trajectory of the given tooth taking into account both the efficiency requirement of minimizing the overall duration of the orthodontic treatment of the subject; and the safety requirement aimed at preventing damages to the subject's teeth.

More specifically, the developers have appreciated that the tooth trajectory may be represented by a plurality of segments, wherein a given segment corresponds to a predetermined treatment interval and may be generated based on applying a specifically determined force (referred to herein as "valid force"), which respects both the Efficiency and the Safety requirements, causing the given tooth to move towards the aligned position.

Thus, non-limiting embodiments of the present technology are directed to determining a valid force to be applied to the given tooth taking onto account the above requirements. In this regard, the Safety requirement may be met by determining the valid force based on a stress value range applicable to a periodontal ligament (PDL) of the given tooth. The non-limiting embodiments of the present technology are further based on a premise that the stress value range has been predetermined for the given tooth such that (1) a minimum value thereof is indicative of a minimum amount of stress applied to the PDL that causes the given tooth to move; whereas (2) a maximum value thereof is indicative of amount of stress, beyond which a permanent damage to the PDL of the given tooth may be caused. Tus, determining the valid force considering the stress value range may ensure avoiding damages to the PDL, such as root resorption, damages to the proximal blood vessels and nerve pathways, for example.

Further, the developers have realized that the safety requirement may be met if collisions of the given tooth with an adjacent tooth are minimized as the collisions therebetween may result in causing discomfort to the subject, or even teeth damage such as chips and cracks of the teeth enamel, for example. Thus, the valid force, considering the stress value range, may further be determined to cause the given tooth to move towards the aligned position with minimum occurrences or extents of respective collisions of the given tooth with the adjacent tooth.

At the same time, the developers have set out to solve an optimization task directed to selecting the valid force in such a way that it allows for satisfying the above considerations in respect of the Safety requirement while causing a maximum possible displacement of the given tooth along the given segment of the tooth, thereby fulfilling the efficiency requirement.

Thus, the non-limiting embodiments of the present technology are directed to methods and systems for determining the valid force to be applied to the given tooth for generating the given segment of the tooth trajectory, such that, having been selected based on the stress value range associated with the given tooth, the valid force causes the maximum possible displacement of the given tooth provided that extents of the collisions between the given tooth and the adjacent tooth are minimized. By so doing, embodiments of the methods and systems described herein, while avoiding or minimizing possible damages to the PDL of the given tooth, are directed to minimizing a number of segments forming the tooth trajectory, thereby reducing the overall duration of the orthodontic treatment. This may translate to a fewer number of associated aligners to be applied to the subject's teeth in the course of the so planned orthodontic treatment. Therefore, these methods and systems allow for determining more effective, efficient, and safer orthodontic treatments.

More specifically, according to a first broad aspect of the present technology, there is provided a method for determining a tooth trajectory for a given tooth of a subject. The tooth trajectory defines movements of the given tooth during an orthodontic treatment. The method is executable by a processor of an electronic device. The method comprises: acquiring a 3D model of an arch form associated with the subject, the 3D model of the arch form including 3D models of a plurality of subject's teeth including a 3D model of the given tooth; identifying an initial position of the given tooth from the 3D model of the given tooth; acquiring an indication of a target position of the given tooth; acquiring a stress values range for stress applicable to the given tooth for causing the given tooth to move from the initial position to the target position, the stress values range including: a minimum stress value being indicative of a minimum amount of stress for causing the given tooth to move; a maximum stress value being indicative of a minimum amount of stress causing permanent damage to the given tooth; generating, based on the 3D model of the given tooth, a plurality of segments defining the tooth trajectory of the given tooth from the initial position to the target position, a given segment of the plurality of segments being associated with a start position and with an end position, the given segment of the plurality of segments having been generated by executing an optimization algorithm, the executing comprising: identifying the start position associated with the given segment; applying an initial force to the 3D model of the given tooth, the initial force causing a first maximum displacement, in a predetermined interval, of the 3D model of the given tooth from the start position associated with the given segment towards the target position associated with the given tooth; determining, from the first maximum displacement, if there is an occurrence of a collision between the 3D model of the given tooth and a 3D model of at least one adjacent tooth, the collision being caused by applying the initial force; in response to determining that there is the occurrence of the collision, iteratively optimizing, based on the stress values range, the initial force, until: a second maximum displacement of the 3D model of the given tooth is caused, by an optimized initial force, in the predetermined interval, from the start position associated with the given segment towards the target position associated with the given tooth provided that an extent of the collision between the 3D model of the given tooth and the 3D model of the at least one adjacent tooth is minimized; determining the optimized initial force as being a valid force to be applied to the given tooth, thereby identifying the end position associated with the given segment; storing data indicative of the given segment; and using the tooth trajectory for the given tooth for planning the orthodontic treatment of the subject.

In some implementations of the method, the applying the initial force causes respective collisions among at least some other of the 3D models of the plurality of subject's teeth including the 3D model of the given tooth; and the method further comprises: in response to determining an occurrence of at least one of the respective collisions, iteratively optimizing the initial force until a third maximum displacement of the 3D model of the given tooth is caused, by an optimized initial force, in the predetermined interval, from the start position associated with the given segment towards the target position associated with the given tooth provided that an extent of the at least one of the respective collisions is minimized; and determining the optimized initial force as being the valid force to be applied to the given tooth.

In some implementations of the method, an extent of a given collision is indicative of a degree of an overlap region between a pair of 3D models of adjacent teeth of the at least some other of the 3D models of the plurality of subject's teeth including the 3D model of the given tooth.

In some implementations of the method, each occurrence of collision is determined by a collision detection algorithm.

In some implementations of the method, in response to determining that there is no occurrence of the collision, the method further comprises determining the initial force as being the valid force to be applied to the given tooth, thereby identifying the end position associated with the given segment based on the first maximum displacement of the 3D model of the given tooth.

In some implementations of the method, the second maximum displacement of the 3D model of the given tooth causes application of respective forces to at least some other of the 3D models of the plurality of subject's teeth, and wherein: each one of the respective forces is determined based on the valid force using a Displacement Response Force Distribution function such that: each one of the respective forces corresponds to a respective stress values range having been predetermined for a respective one of the at least some other of the plurality of subject's teeth.

In some implementations of the method, the given segment defines a movement path for the given tooth during the predetermined interval of the orthodontic treatment, and wherein each one of the plurality of segments of the tooth trajectory defines a respective movement path for the given tooth during a respective one of a plurality of predetermined intervals forming a total duration of the orthodontic treatment.

In some implementations of the method, each one of the plurality of predetermined intervals is equal.

In some implementations of the method, the method further comprises generating, by the optimization algorithm, respective tooth trajectories for other ones of the plurality of subject's teeth, and wherein the orthodontic treatment is representable by a schedule defining movements of each one of the plurality of subject's teeth during respective ones of the plurality of predetermined intervals.

In some implementations of the method, the orthodontic treatment includes applying a respective aligner during each one of the plurality of predetermined intervals.

In some implementations of the method, the method further comprises: in response to modifying the tooth trajectory associated with the given tooth, thereby determining a new tooth trajectory therefor, the modifying causing respective collisions between at least some other of the 3D models of the plurality of subject's teeth including the 3D model of the given tooth; re-generating, by the optimization algorithm, based on the new tooth trajectory for the given tooth, trajectories respectively associated with the at least some other of the plurality of subject's teeth.

In some implementations of the method, the optimization algorithm is configured to generate the given segment to be a line segment.

In some implementations of the method, the stress value range associated with the given tooth has been predetermined using a Stress Distribution Cumulative function.

In some implementations of the method, the optimization algorithm comprises a gradient descent algorithm.

In accordance with a second broad aspect of the present technology, there is provided a system for determining a tooth trajectory for a given tooth of a subject. The tooth trajectory defines movements of the given tooth during an orthodontic treatment. The system comprises a processor of an electronic device configured to execute a method. The method comprises: acquiring a 3D model of an arch form associated with the subject, the 3D model of the arch form including 3D models of a plurality of subject's teeth including a 3D model of the given tooth; identifying an initial position of the given tooth from the 3D model of the given tooth; acquiring an indication of a target position of the given tooth; acquiring a stress values range for stress applicable to the given tooth for causing the given tooth to move from the initial position to the target position, the stress values range including: a minimum stress value being indicative of a minimum amount of stress for causing the given tooth to move; a maximum stress value being indicative of a minimum amount of stress causing permanent damage to the given tooth; generating, based on the 3D model of the given tooth, a plurality of segments defining the tooth trajectory of the given tooth from the initial position to the target position, a given segment of the plurality of segments being associated with a start position and with an end position, the given segment of the plurality of segments having been generated by executing an optimization algorithm, the executing comprising: identifying the start position associated with the given segment; applying an initial force to the 3D model of the given tooth, the initial force causing a first maximum displacement, in a predetermined interval, of the 3D model of the given tooth from the start position associated with the given segment towards the target position associated with the given tooth; determining, from the first maximum displacement, if there is an occurrence of a collision between the 3D model of the given tooth and a 3D model of at least one adjacent tooth, the collision being caused by applying the initial force; in response to determining that there is the occurrence of the collision, iteratively optimizing, based on the stress values range, the initial force, until: second maximum displacement of the 3D model of the given tooth is caused, by an optimized initial force, in the predetermined interval, from the start position associated with the given segment towards the target position associated with the given tooth provided that an extent of the collision between the 3D model of the given tooth and the 3D model of the at least one adjacent tooth is minimized; determining the optimized initial force as being a valid force to be applied to the given tooth, thereby identifying the end position associated with the given segment; storing data indicative of the given segment; and using the tooth trajectory for the given tooth for planning the orthodontic treatment of the subject.

In some implementations of the system, the applying the initial force causes respective collisions among at least some other of the 3D models of the plurality of subject's teeth including the 3D model of the given tooth, and the processor is further configured to: in response to determining an occurrence of at least one of the respective collisions, iteratively optimizing the initial force until a third maximum displacement of the 3D model of the given tooth is caused, by an optimized initial force, in the predetermined interval, from the start position associated with the given segment towards the target position associated with the given tooth provided that an extent of the at least one of the respective collisions is minimized; and determining the optimized initial force as being the valid force to be applied to the given tooth.

In some implementations of the system, an extent of a given collision is indicative of a degree of an overlap region between a pair of 3D models of adjacent teeth of the at least some other of the 3D models of the plurality of subject's teeth including the 3D model of the given tooth.

In some implementations of the system, to determine each occurrence of collision, the processor is configured to apply a collision detection algorithm.

In some implementations of the system, the second maximum displacement of the 3D model of the given tooth causes application of respective forces to at least some other of the 3D models of the plurality of subject's teeth, and wherein: each one of the respective forces is determined based on the valid force using a Displacement Response Force Distribution function such that: each one of the respective forces corresponds to a respective stress values range having been predetermined for a respective one of the at least some other of the plurality of subject's teeth.

In some implementations of the system, the given segment defines a movement path for the given tooth during the predetermined interval of the orthodontic treatment, and wherein each one of the plurality of segments of the tooth trajectory defines a respective movement path for the given tooth during a respective one of a plurality of predetermined intervals forming a total duration of the orthodontic treatment; and the processor is further configured to: generate, by the optimization algorithm, respective tooth trajectories for other ones of the plurality of subject's teeth, and wherein the orthodontic treatment is representable by a schedule defining movements of each one of the plurality of subject's teeth during respective ones of the plurality of predetermined intervals; in response to modifying the tooth trajectory associated with the given tooth, thereby determining a new tooth trajectory therefor, the modifying causing respective collisions between at least some other of the 3D models of the plurality of subject's teeth including the 3D model of the given tooth; re-generate, by the optimization algorithm, based on the new tooth trajectory for the given tooth, trajectories respectively associated with the at least some other of the plurality of subject's teeth.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
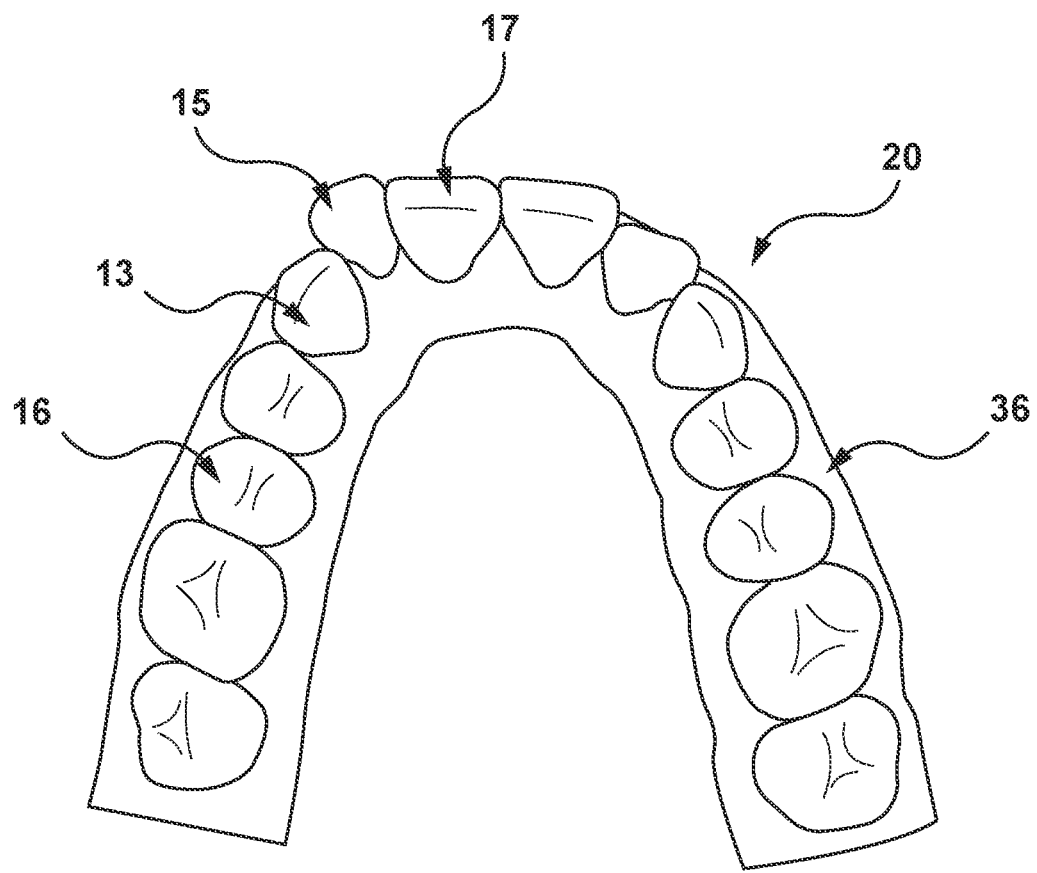
FIG. 1 depicts a bottom view of an upper arch form of a subject exemplifying a misalignment of some of subject's teeth, in accordance with certain non-limiting embodiments of the present technology.

Certain aspects and embodiments of the present technology are directed to methods of and systems for developing a more efficient orthodontic treatment for a subject (also referred to herein as a "patient"), which also considers certain safety constraints.

Further, it should be expressly understood that, in the context of the present specification, the term "orthodontic treatment" is broadly referred to as any type of medical intervention aimed at correcting malocclusions associated with the teeth of the patient, including surgical and non-surgical manipulations, such as, but not limited to, using one or more of aligners, brackets, multi-strand wires, strips, retainers, and plates. Further, the orthodontic treatment, as referred to herein, may be determined automatically by a specific software, based on respective image data and input parameters associated with the subject, or semi-automatically with input from a professional practitioner in the field of dentistry (such as an orthodontist, a maxillofacial surgeon, for example).

More specifically, certain aspects and embodiments of the present technology comprise a computer-implemented method for determining forces to be applied to the given tooth, based on a 3D model thereof, in the course of the orthodontic treatment. In certain aspects and embodiments of the present technology, modulating magnitudes and directions of these forces for (1) minimizing extents of potential collisions between the given tooth and at least one of adjacent teeth, and (2) satisfying safety constraints in respect of a level of stress applied to a periodontal ligament (PDL) surrounding the given tooth, while (3) causing a maximum displacement thereof towards an aligned position within a subject's arch form may achieve safer and more efficient orthodontic treatments for the subject.

Certain non-limiting embodiments of the present technology minimize, reduce or avoid some of the problems noted in association with the prior art. For example, by implementing certain embodiments of the present technology in respect of determining the tooth trajectory for the given tooth, the following advantages may be obtained: modelling more efficient and safer tooth movements of the given tooth in the course of the orthodontic treatment. This is achieved, in certain non-limiting embodiments of the present technology, by (1) selecting a given force based on a range of admissible stress applicable to the PDL without causing permanent damage thereto, and (2) optimizing the given force for causing the given tooth to perform a maximum possible displacement provided that a number or an extent of collisions with the adjacent teeth is minimized. In this regard, methods and systems provided herein, according to certain non-limiting embodiments of the present technology, allow reducing an overall duration of the orthodontic treatment and, at the same time, increasing safety thereof. For example, reducing the overall duration of the orthodontic treatment may be achieved by applying a fewer number of orthodontic devices (such as aligners) causing respective tooth movements of the given tooth towards the aligned position.

Orthodontic Treatment

Referring initially to FIG. 1, there is depicted a bottom view of an upper arch form 20 of the subject, to which certain aspects and non-limiting embodiments of the present technology may be applied.

As it can be appreciated, the upper arch form 20 includes upper teeth 16 and an upper gingiva 36. Further, in the depicted embodiments of FIG. 1, a tooth 15 is misaligned within the upper teeth 16 as it protrudes outwardly relative to its neighboring teeth, a first adjacent tooth 13 and a second adjacent tooth 17. Thus, for correcting the present misalignment of the tooth 15, an orthodontic treatment may be provided to the subject.

In accordance with certain non-limiting embodiments of the present technology, the orthodontic treatment may comprise applying an orthodontic device. Generally speaking, the orthodontic device may be configured to exert a force onto the tooth 15 causing it to move towards an aligned position, that is, in the depicted embodiments of FIG. 1, inwardly between the first adjacent tooth 13 and the second adjacent tooth 17 to align with the first adjacent tooth 13 and the second adjacent tooth 17. In various non-limiting embodiments of the present technology, the orthodontic device may comprise orthodontic appliances of different types, shapes, sizes and configurations, such as those including, without limitation, aligners, brackets, multi-strand wires, strips, retainers, and plates.

Figure 2A:
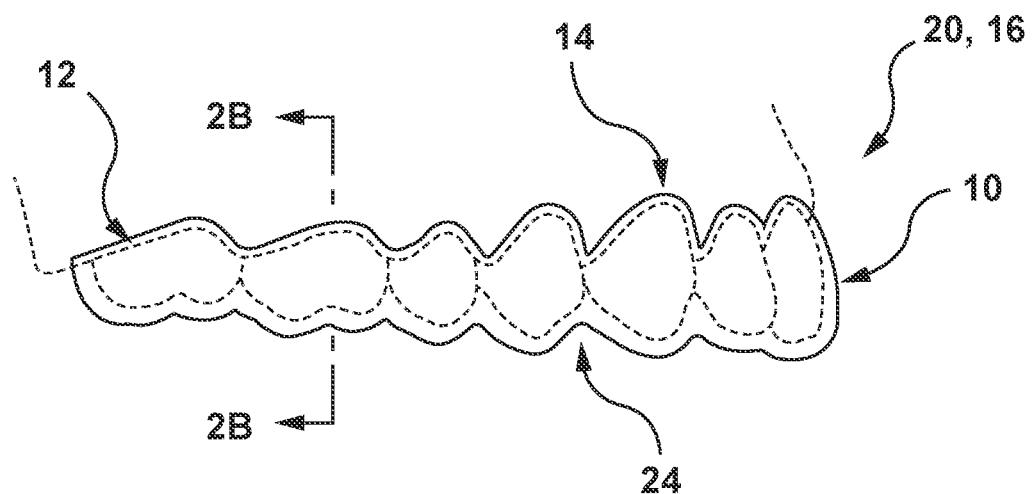
FIGS. 2A and 2B depict side and cross-sectional views, respectively, of a personalized dental appliance applied to subject's teeth that may be configured to treat the misalignment of the subject's teeth present in FIG. 1, in accordance with certain non-limiting embodiments of the present technology.
Figure 2B:
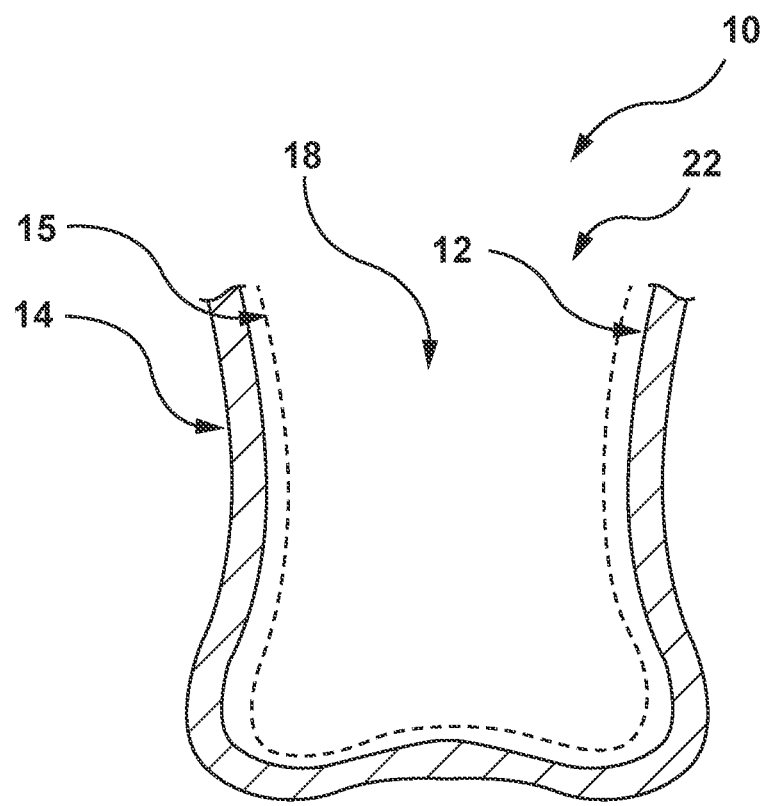

In specific non-limiting embodiments of the present the present technology, the orthodontic device may include an aligner. With reference to FIGS. 2A and 2B, there is depicted an aligner 10 applied to at least some of the upper teeth 16, in accordance with certain non-limiting embodiments of the present technology. The aligner 10 comprises an inner surface 12 and an outer surface 14. The inner surface 12 defines a channel 18, which is configured, in some non-limiting embodiments of the present technology, for receiving crown portions of at least some of the upper teeth 16 including the tooth 15, the first adjacent tooth 13, and the second adjacent tooth 17. However, in other non-limiting embodiments of the present technology, the channel 18 of the aligner 10 may be configured to receive crown portions of all of the upper teeth 16. At least one edge of the channel 18 is shaped for following a gum line 22 along the upper gingiva 36.

In accordance with the non-limiting embodiments of the present technology, a size, a form factor (such as a U-shape or a V-shape, for example), and a configuration of the aligner 10, including a material and a thickness thereof, depend generally on a particular malocclusion disorder of the subject (such as the misalignment of the tooth 15 within the upper teeth 16), at which the orthodontic treatment is aimed. However, as an example, in some non-limiting embodiments of the present technology, the thickness of the aligner 10 may be about 0.7 mm. In other non-limiting embodiments of the present technology, the thickness is selected from 0.7 mm, 0.75 mm, 0.8 mm, 0.85 mm, 0.9 mm, 0.95 mm, and 1.0 mm. In yet other non-limiting embodiments of the present technology, the aligner 10 may have regions of variable thickness, such as in interdental regions 24, as an example.

According to certain non-limiting embodiments of the present technology, the aligner 10 may be made of a polymer, such as a thermoplastic material. In other non-limiting embodiments of the present technology, the aligner 10 may be made of poly-vinyl chloride (PVC). In yet other non-limiting embodiments of the present technology, the aligner 10 may be made of polyethylene terephthalate glycol (PETG). Other suitable materials can also be used to form the aligner 10.

It is appreciated that, in accordance with certain non-limiting embodiments of the present technology, the aligner 10 may be used for treating different types of teeth misalignment or malocclusion, including but not limited to one or more of: closing gaps ("space closure"), creating/widening gaps, tooth rotation, tooth intrusion/extrusion, and tooth translation, to name a few. It should further be noted that in certain non-limiting embodiments of the present technology, applying the aligner 10 to the upper teeth 16 may further include applying specific attachments (also known as "fixing blocks") thereto.

As it may become apparent, the aligner 10, may be designed in such a way that its current configuration is representative of a desired position of the upper teeth 16 at a given stage of the orthodontic treatment, which thus allows, due to stiffness properties of the material of the aligner 10, imposing a respective force onto each crown portion of a respective one of the upper teeth 16 appointed for the orthodontic treatment.

Thus, referring back to FIG. 1, in order to cause the tooth 15 to reach the aligned position, first, various configurations of the aligner 10 may be used to sequentially move each one of the upper teeth 16 before the tooth 15 downwardly (in the orientation of FIG. 1), thereby preparing space therefor to be further moved inwardly. Second, the aligner 10 may be configured to cause the tooth 15 to move inwardly, towards the aligned position thereof within the upper teeth 16.

Figure 6:
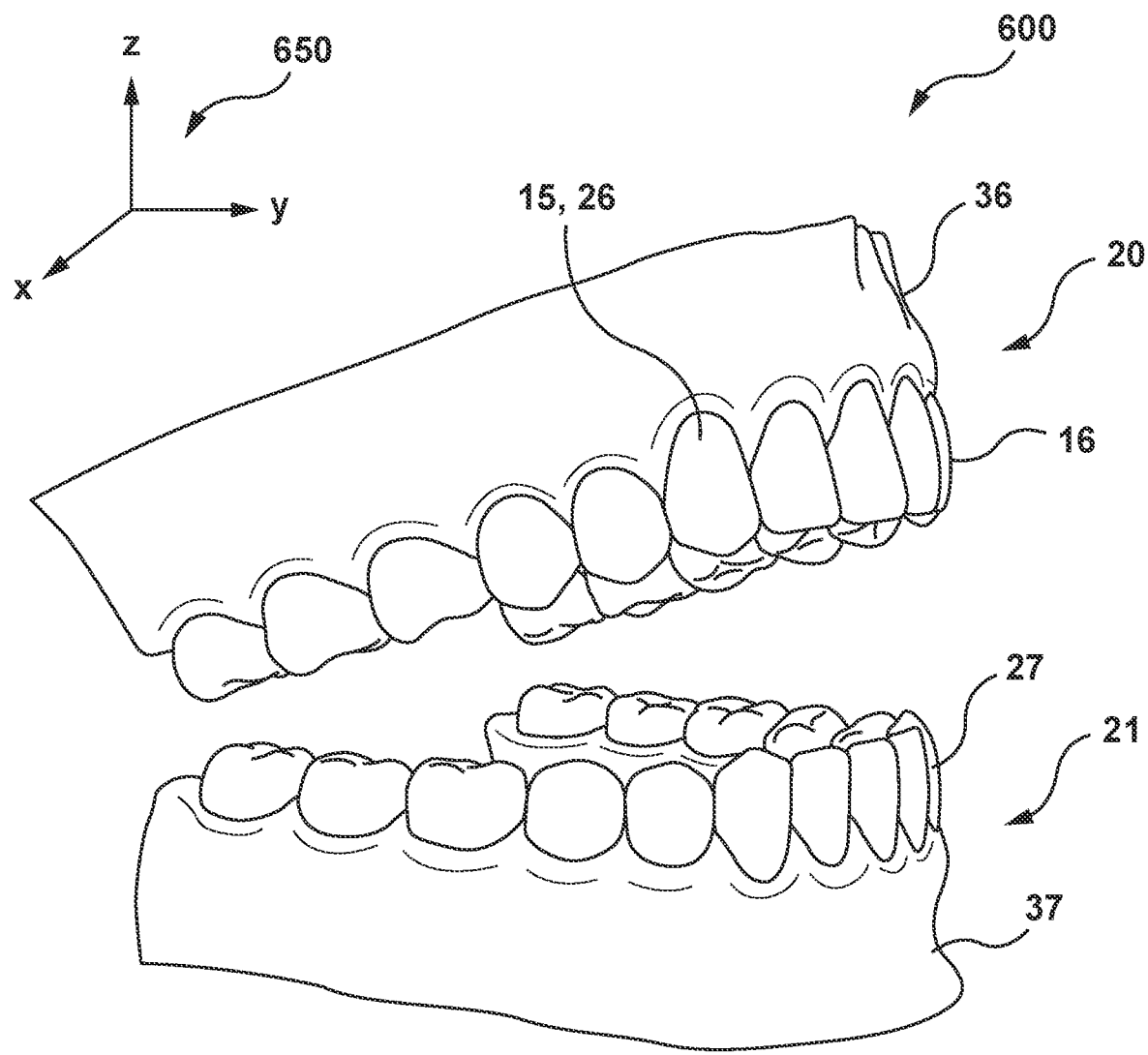
FIG. 6 depicts a perspective view of a 3D model of the upper arch form and a lower arch form of the subject of FIG. 1, in accordance with the non-limiting embodiments of the present technology.

Needles to say that, although in the depicted embodiments of FIGS. 2A and 2B, the aligner 10 is configured to be applied onto the upper teeth 16, in other non-limiting embodiments of the present technology, a certain configuration of the aligner 10 may be applied to teeth of a lower arch form (such as a lower arch form 21, 3D representation of which is depicted in FIG. 6) of the subject aimed at respective malocclusion disorders.

Figure 3B:
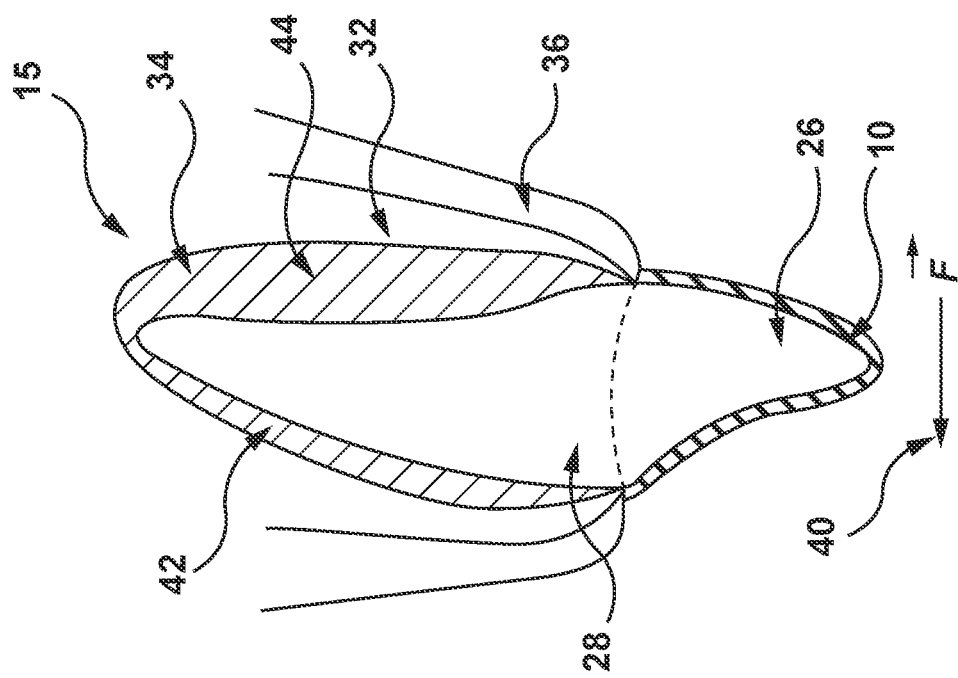
FIGS. 3A and 3B schematically depict internal anatomy of a given one of the subject's teeth present in FIG. 1 with and without application of the personalized dental appliance of FIGS. 2A and 2B, respectively, in accordance with certain non-limiting embodiments of the present technology.

Biomechanical processes allowing a given one of the upper teeth 16 to move in the course of the orthodontic treatment, such as the tooth 15 towards the aligned position, under the respective force imposed by the aligner 10 will now be described with reference to FIGS. 3A and 3B.

Figure 3A:
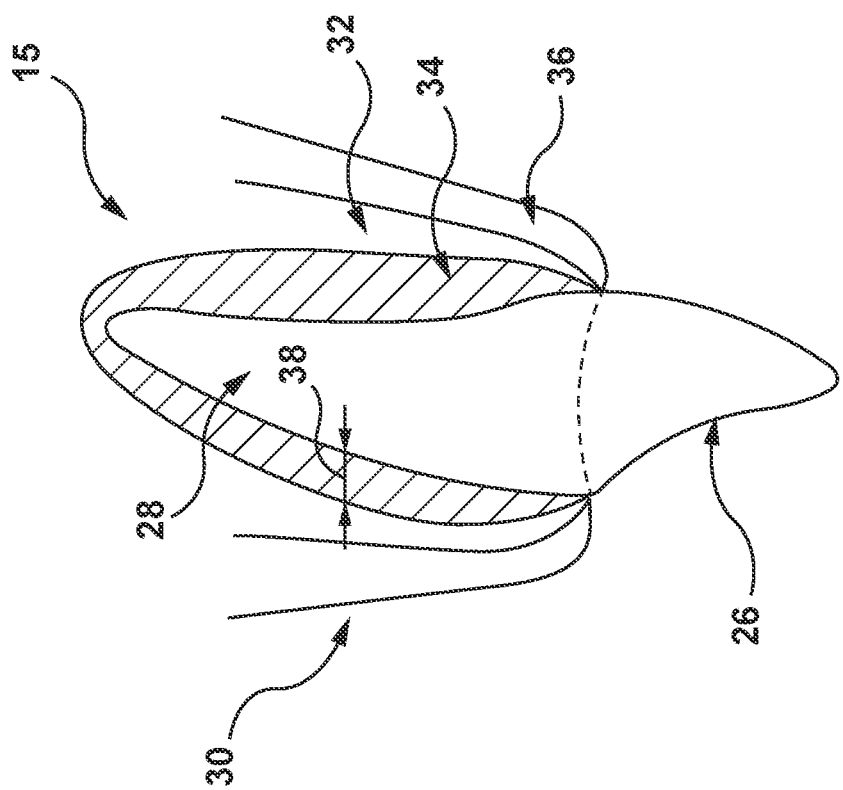

With reference to FIG. 3A, there is depicted a cross-sectional view of the tooth 15 schematically illustrating some of surroundings tissues thereof, in accordance with certain non-limiting embodiments of the present technology. FIG. 3B depicts the same cross-sectional view of the tooth 15 with the aligner 10 applied thereto.

The tooth 15 includes a crown portion 26 and a root portion 28. Tissues of a periodontium 30 surrounding and supporting the upper teeth 16, and the tooth 15, in particular, include the upper gingiva 36, an alveolar bone 32, and a periodontal ligament (PDL) 34. The PDL 34 surrounds the root portion 28 and attaches the tooth 15 to the alveolar bone 32. As it can be appreciated from FIG. 3B, the aligner 10 causes a force 40 to be applied to the crown portion 26 of the tooth 15, which may cause compression of the PDL 34 on a compressed portion 42 of the root portion 28, and tension of the PDL 34 on a strained portion 44 of the root portion 28. Accordingly, during a predetermined treatment interval of application of the aligner 10, this may cause remodelling of the alveolar bone 32 surrounding the tooth 15, with bone resorption of the alveolar bone 32 occurring on the compressed portion 42, and bone deposition of the alveolar bone 32 on the strained portion 44. Thus, through this mechanism, the force 40 causes the tooth 15 to be displaced.

As it may become apparent, based on parameters associated with the force 40, such as a magnitude and a direction thereof, a current displacement of the tooth 15 towards the aligned position may be determined. However, there may be certain safety constraints associated with the force 40.

For example, according to certain non-limiting embodiments of the present technology, if the force 40 has the magnitude causing the tooth 15 to displace at longer than a length of a PDL space 38, during the predetermined treatment interval, the force 40 may cause damage to the tissues of the periodontium 30 of the tooth 15, such as resorption of the root portion 28 or excess compression of proximal blood vessels and nerve pathways in the upper gingiva 36 (causing necrosis thereof), as an example.

Further, as another example, the force 40 may have the magnitude and the direction causing movement of the given tooth 15 such that it collides with an adjacent tooth, such as the first adjacent tooth 13 and the second adjacent tooth 17. In this regard, the collision may cause damage to one of the tooth 15 and the at least one of the first adjacent tooth 13 and the second adjacent tooth 17 such as chipping or cracking of respective crown portions, as an example; or may cause discomfort (such as pain) to the subject which may affect adherence thereof to the orthodontic treatment. Additionally, resolving the collision may increase the duration of the orthodontic treatment, which may reduce the efficiency thereof.

Finally, as yet another example, if the magnitude and the direction of the force 40 are selected such that the distance towards the aligned position is fragmented into a plurality of path segments, wherein each path segment is significantly shorter than the length of the PDL space 38, the duration of the orthodontic treatment may be significantly prolonged reducing the efficiency of such an approach.

Thus, non-limiting embodiments of the present technology described herein are directed to optimizing, based on a 3D model of the upper arch form 20, the force 40 taking into account the above safety considerations, while allowing a maximum possible displacement of the tooth 15 towards the aligned position. By doing so, certain embodiments of the present technology generate a safer and more efficient tooth trajectory for the tooth 15 from the current position towards the aligned position. In other words, the methods and systems for planning the orthodontic treatment described herein may allow for decreasing a number of segments of the tooth trajectory minimizing the overall duration of the orthodontic treatment, for example, by minimizing a number of associated aligners to be used therefor, wherein each segment is indicative of a respective maximum displacement of the tooth 15 under the force 40 having the magnitude and direction avoiding collisions of the tooth 15 and damage to the tissues of the periodontium 30.

According to certain non-limiting embodiments of the present technology, examples of the damage to the tissues of the periodontium 30 are not limited and may include, for example, root resorption of the root portion 28; pain associated with the application of the force 40, pulpal changes in the tooth 15; periodontal disease associated with the tooth 15, such as gingivitis, loss of the alveolar bone 32, periodontitis, and the like; and decalcification of enamel of the crown portion 26, to name a few. This damage may be temporary, that is, may be resolved, for example, by applying a respective treatment in a finite period (such as weeks, months, or even years depending on a specific case), or permanent, that is, may not be reversed by any currently known treatment.

How the tooth trajectory is generated and how it may be used for planning the orthodontic treatment, according to certain non-limiting embodiments of the present technology, will be described with reference to FIGS. 8 to 12.

System

Figure 4:
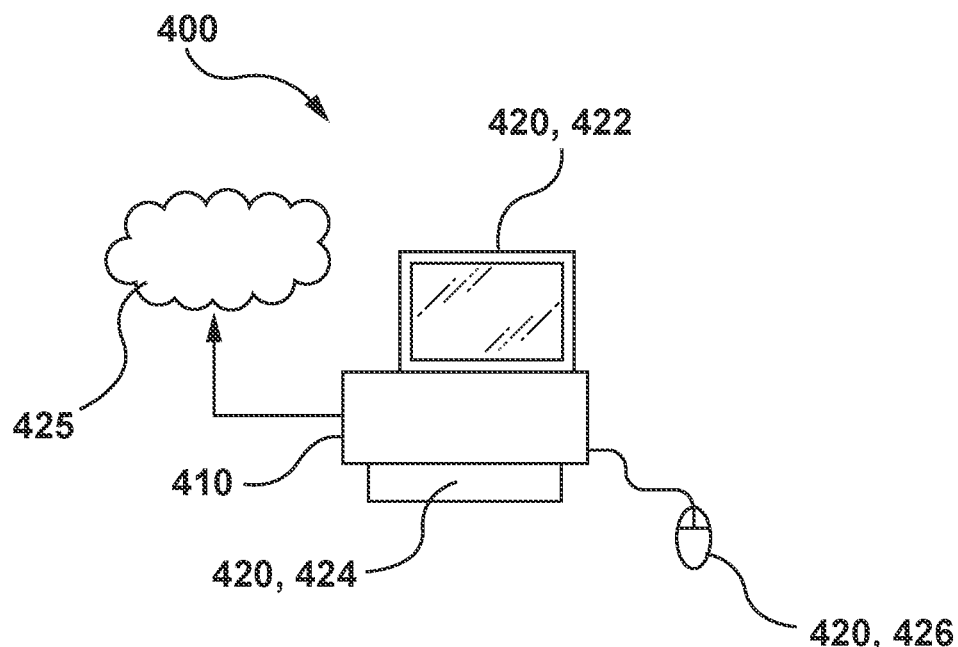
FIG. 4 depicts a schematic diagram of a system for planning an orthodontic treatment, in accordance with certain embodiments of the present technology.
Figure 5:
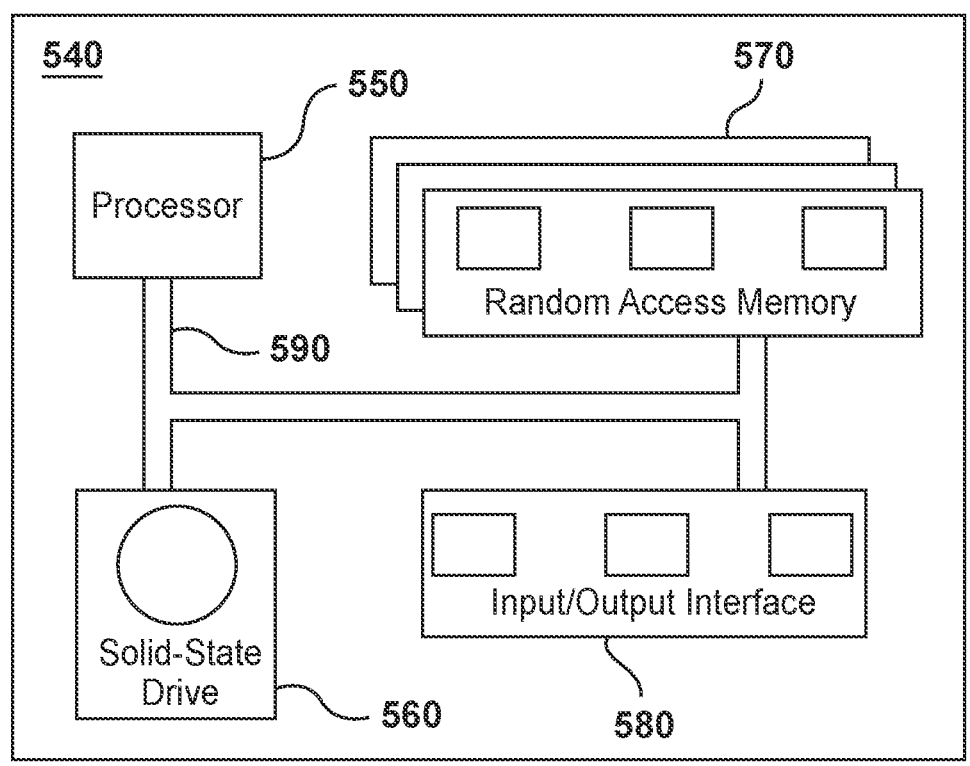
FIG. 5 depicts a schematic diagram of a computing environment of the system of FIG. 4, in accordance with certain embodiments of the present technology.

Referring to FIGS. 4 and 5, there is depicted a schematic diagram of a system 400 suitable for determining the tooth trajectory for planning the orthodontic treatment, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to generate, based on image data associated with the subject, a plurality of segments indicative of tooth movements of the tooth 15, thereby defining the tooth trajectory thereof, according to certain non-limiting embodiments of the present technology. In some non-limiting embodiments of the present technology, the computer system 410 may further be configured to determine, based at least on the tooth trajectory of the tooth 15, the orthodontic treatment for the subject, as will be described further.

To that end, in some non-limiting embodiments of the present technology, the computer system 410 is configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 410 may be configured to receive the image data associated with the subject directly from an imaging device 430 communicatively coupled thereto. Broadly speaking the imaging device 430 may be configured (for example, by a processor 550 depicted in FIG. 5) to capture and/or process the image data of the upper teeth 16 and the periodontium (not depicted) of the subject. In certain non-limiting embodiments of the present technology, the image data may include, for example, one or more of: (1) images of external surfaces of respective crown portions (such as the crown portion 26 of the tooth 15) of the upper teeth 16, (2) images of an external surface of the periodontium including those of the upper gingiva (not depicted), the alveolar maxillary bone (not depicted), and images of superficial blood vessels and nerve pathways associated with the upper teeth 16; and (3) images of an oral region. By doing so, the imaging device 430 may be configured, for example, to capture image data of the upper arch form 20 of the subject. In another example, the imaging device may also be configured to capture and/or process image data of a lower arch form (such as the lower arch form 21 depicted in FIG. 6) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of the upper arch form 20 of the subject.

In a specific non-limiting example, the intraoral scanner can be of one of the types available from MEDIT, corp. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 430 may comprise a desktop scanner enabling to digitize a mold representing the upper arch form 20. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from Dental Wings, Inc. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 430 may comprise a cone beam computed tomography (CBCT) scanner. Generally speaking, the CBCT scanner comprises software and hardware allowing for capturing data using a cone-shaped X-ray beam by rotating around the subject's head. This data may be used to reconstruct 3D representations of the following regions of the subject's anatomy: dental (teeth and gum, for example); oral and maxillofacial region (mouth, jaws, and neck), and ears, nose, and throat ("ENT").

In a specific non-limiting example, the CBCT scanner can be of one of the types available from 3Shape, Private Limited Company of Holmens Kanal 7, 1060 Copenhagen, Denmark. It should be expressly understood that the CBCT scanner can be implemented in any other suitable equipment.

Further, it is contemplated that the computer system 410 may be configured for processing of the received image data. The resulting image data of the upper arch form 20 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

With reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random access memory 570 and an input/output interface 580. Communication between the various components of the computing environment 540 may be enabled by one or more internal and/or external buses 590 (e.g. a PCI bus, universal serial bus, IEEE 1394 "Firewire" bus. SCSI bus. Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 560 stores program instructions suitable for being loaded into the random access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As previously alluded to, according to the non-limiting embodiments of the present technology, the processor 550 may be configured to: (1) receive the image data associated with the subject's teeth (such as the upper teeth 16), (2) based on the received image data, determine, for at least some of the upper teeth 16, a respective tooth trajectory, for example, the tooth trajectory of the tooth 15; and (3) based on the so determined tooth trajectories, determine the orthodontic treatment for the subject.

According to some non-limiting embodiments of the present technology, having received the image data, the processor 550 may be configured to generate 3D models of arch forms of the subject.

With reference to FIG. 6, there is depicted a perspective view of a 3D model 600 representing a current configuration of the upper arch form 20 (also referred to herein as "maxillary arch form") and the lower arch form 21 (also referred to herein as "mandibular arch form") of the subject, in accordance with the non-limiting embodiments of the present technology.

According to the non-limiting embodiments of the present technology, the upper arch form 20 comprises the upper teeth 16 (also referred to herein as "maxillary teeth") and the upper gingiva 36, and the lower arch form 21 comprises lower teeth 27 (also referred to herein as "mandibular teeth") and a lower gingiva 37. As it can be appreciated, the upper teeth 16 and the lower teeth 27 are represented, in the 3D model 600, by respective crown portions associated therewith, such as the crown portion 26 of the tooth 15.

Further, according to certain non-limiting embodiments of the present technology, the processor 550 may be configured to determine a coordinate system 650 associated with the 3D model 600. In one non-limiting example, the processor 550 may be configured to determine the coordinate system 650 such that an XY plane thereof is parallel to a transverse plane associated with a subject's skull (not depicted). In another example, the XY plane may be parallel to a Frankfort horizontal plane associated with the subject's cranium (not depicted).

In some non-limiting embodiments of the present technology, after receiving the 3D model 600, the processor 550 may be configured to segment thereon 3D representations of crown portions associated with the respective teeth from each other as well as from an associated gingiva, thereby generating a plurality of so segmented crown portions associated with one of the upper arch form 20 and the lower arch form 21 of the subject. To that end, according to some non-limiting embodiments of the present technology, the processor 550 may be configured to apply one or more approaches to automatic tooth segmentation, for example, one, which is described in a co-owned U.S. patent application Ser. No. 16/703,471, entitled "METHOD AND SYSTEM FOR DENTAL BOUNDARY DETERMINATION", and; the content of which is hereby incorporated by reference in its entirety.

In additional non-limiting embodiments of the present technology, for a more effective modeling of the movements of the tooth 15 by applying respective forces thereto (such as the force 40) in the course of the orthodontic treatment, the processor 550 may be configured to augment the 3D model 600, which may include, for example: (1) reconstructing a 3D representation of the root portion 28 (for example, in those embodiments where the imaging device 430 is the intra-oral scanner used for generating the 3D model 600); (2) augmenting a 3D representation of the crown portion 26, further including, for example, reconstructing an accurate contour thereof; and (3) reconstructing an augmented ginigva 3D representation (not depicted) of the upper gingiva 36 corresponding to actual dimensions thereof. To that end, according to certain non-limiting embodiments of the present technology, the processor 550 may be configured to apply one of tooth reconstruction techniques described in a co-owned U.S. patent application Ser. No. 16/936,937 filed on Jul. 23, 2020, entitled "SYSTEMS AND METHODS FOR PLANNING AN ORTHODONTIC TREATMENT", and, the content of which is incorporated hereby by reference.

Figure 7:
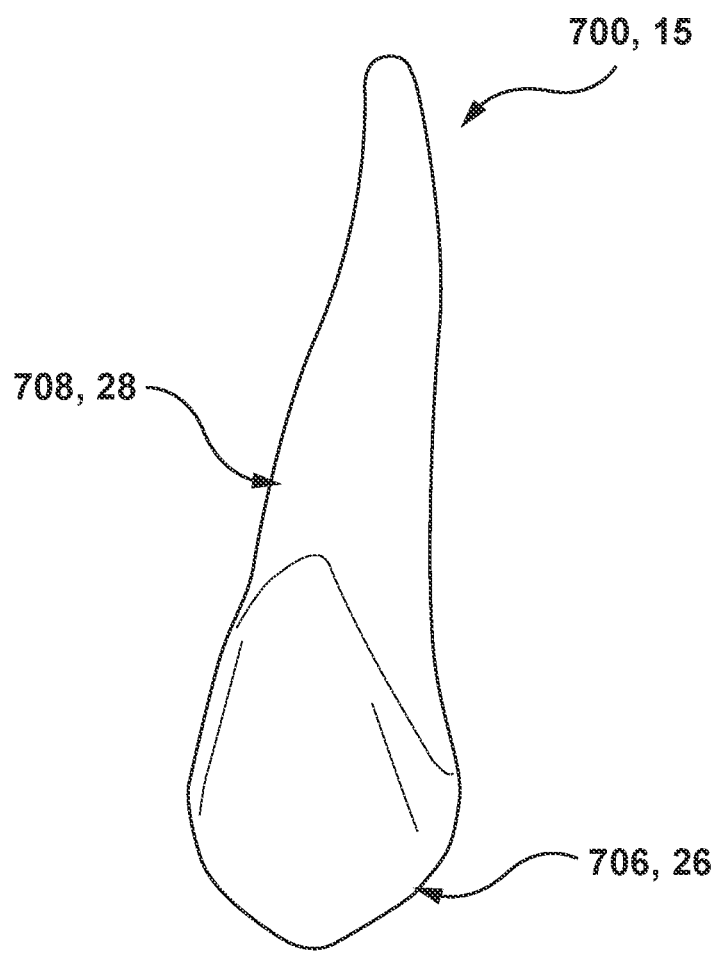
FIG. 7 depicts a 3D model of the given one of the subject's teeth of FIGS. 3A and 3B used, by the processor of FIG. 5, for generating a respective tooth trajectory, in accordance with the non-limiting embodiments of the present technology.

With reference to FIG. 7, there is depicted a tooth 3D representation 700 of the tooth 15 generated by the processor 550 based on the 3D model 600 of FIG. 6, in accordance with certain non-limiting embodiments of the present technology. As it can be appreciated, the tooth 3D representation 700 includes a crown 3D representation 706 of the crown portion 26 and a root 3D representation 708 of the root portion 28. Accordingly, the processor 550 may be configured to use the tooth 3D representation 700 for modelling force application to the tooth 15, thereby generating its trajectory including its movements and positions within the upper arch form 20 in the course of the orthodontic treatment.

In additional non-limiting embodiments of the present technology, the processor 550 may be configured to determine, in order to model various movements of the tooth 15 based on the forces applied to the tooth 3D representation 700, a tooth axis and a center of resistance point associated with the tooth 15. To that end, the processor 550 may be configured to apply to the tooth 3D representation 700 one of method described in a co-owned U.S. patent application Ser. No. 16/877,972, entitled "SYSTEMS AND METHODS FOR DETERMINING TOOTH CENTER OF RESISTANCE", and; the content of which is hereby incorporated by reference in its entirety.

Thus, the processor 550 may be configured to generate separate 3D representations of each of the upper teeth 16 for modelling movements thereof by applying the respective forces thereto in order to generate respective tooth trajectories used for planning the orthodontic treatment for the subject.

According to certain non-limiting embodiments of the present technology, as previously mentioned, the tooth trajectory for the tooth 15 may comprise a plurality of segments, each of which being indicative of a respective displacement of the tooth 15 towards the aligned position during the planned orthodontic treatment.

Figure 8:
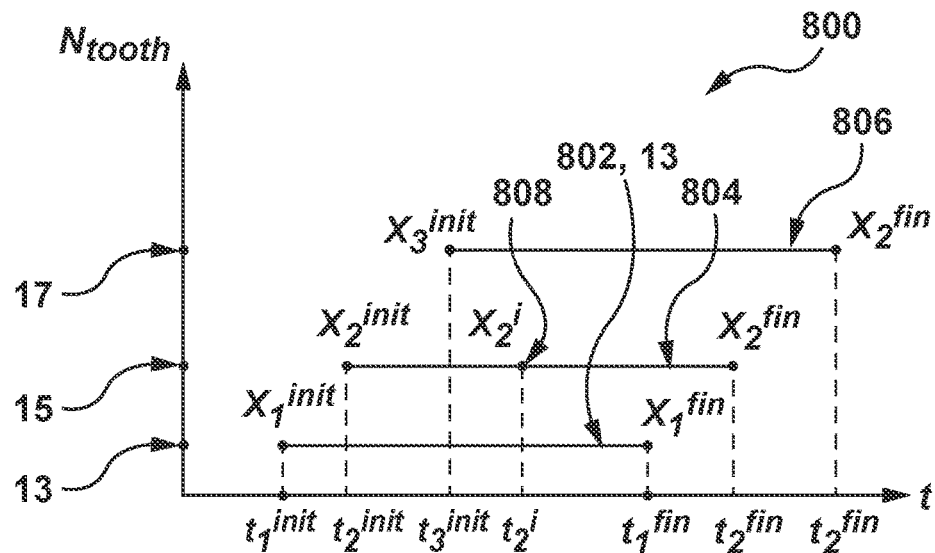
FIG. 8 depicts a schematic diagram of a schedule used, by the processor of FIG. 5, for generating respective trajectories for the at least some of the subject's teeth present in FIG. 1, in accordance with certain non-limiting embodiments of the present technology.

With reference to FIG. 8, there is provided a schematic diagram of a schedule 800 used, by the processor 550, to determine trajectories of some of the upper teeth 16, such as the tooth 15, the first adjacent tooth 13, and the second adjacent tooth 17, for planning the orthodontic treatment, in accordance with certain non-limiting embodiments of the present technology.

As it can be appreciated from the schedule 800, each one of a first trajectory 802, a second trajectory 804, and a third trajectory 806 defining movements of the first adjacent tooth 13, the tooth 15, and the second adjacent tooth 17, respectively, is associated with at least two moments in time: (1) an initial moment in time $t_j^{init}$ associated with a respective initial position of the tooth 15, the first adjacent tooth 13, and the second adjacent tooth 17 within the upper arch form 20, which, for example, may be representative of the current configuration of the these teeth as depicted in FIG. 1; and (2) a final moment in time $t_j^{fin}$ associated with a respective target position thereof, such as that being indicative of alignment of the tooth 15.

Accordingly, for generating each one of the first trajectory 802, the second trajectory 804, and the third trajectory 806, in certain non-limiting embodiments of the present technology, the processor 550 may be configured to determine, based on the 3D model 600, the respective initial positions of the tooth 15, the first adjacent tooth 13, and the second adjacent tooth 17 within the coordinate system 650 associated with the 3D model 600. In other words, at a given initial moment in time $t_j^{init}$, the processor 550 may be configured to determine 6 degrees of freedom (DOF), $X_j^{init}$, of a respective one of the tooth 15, the first adjacent tooth 13, and the second adjacent tooth 17, thereby identifying the initial position thereof within the upper arch form 20.

Further, according to certain non-limiting embodiments of the present technology, the processor 550 may be configured to acquire 6 DOF, within the coordinate system 650, of a respective target position. $X_j^{fin}$, of each one of the tooth 15, the first adjacent tooth 13, and the second adjacent tooth 17. In some non-limiting embodiments of the present technology, the respective target position for each of the teeth may be provided by the clinician. In other non-limiting embodiments of the present technology, the processor 550 may be configured to determine the respective target positions based on averaged data associated with aligned teeth received from a group of subjects.

Further, as mentioned earlier, a given trajectory, such as the second trajectory 804, may include a plurality of segments. According to some non-limiting embodiments of the present technology, each of the plurality of segments may be generated by optimizing an initial force applied, to the tooth 3D representation 700, by the processor 550 at a respective initial moment in time $t_2^{init}$ to overcome a potential collision of the tooth 3D representation 700 or to adjust the initial force to meet the above-identified safety requirements, as will be described in greater detail below. To that end, the processor 550 may be configured to identify at least one intermediate trajectory point 808 defining an intermediate position of the tooth 3D representation 700 $X_2^i$ associated with an intermediate moment in time $t_2^i$. By doing so, the processor 550 may be configured to determine a plurality of predetermined treatment intervals forming a total duration of the orthodontic treatment. Thus, by way of example, the second trajectory 804 may be represented (other trajectories may be represented similarly) by the plurality of segments forming a totality thereof, where each one of the plurality of segments is associated with a respective one of the plurality of predetermined treatment intervals: $\langle t_2^{init}, X_2^{init}; t_2^{i}, X_2^{i}; t_2^{fin}, X_2^{fin} \rangle$.

Thus, according to certain non-limiting embodiments of the present technology, by applying a respective optimized force to the tooth 3D representation 700 causing a respective displacement thereof along a given one of the plurality of segments, the processor 550 may be configured to identify an end position (such as that corresponding to the at least one intermediate trajectory point 808, $X_2^{i}$) for the given segment of the second trajectory 804. Finally, the processor 550 may be configured to store each optimized force to be further applied to the tooth 15 in the course of the orthodontic treatment.

According to certain non-limiting embodiments of the present technology, the processor 550 may be configured to determine the initial force as being arbitrary, that is, the initial force may violate at least one of the safety requirements, that is, it may cause, when applied to the tooth 15, at least one of: (1) a damage to the tissues of the periodontium 30 of the tooth 15; and (2) at least one collision between the tooth 15 and at least one of the first adjacent tooth 13 and the second adjacent tooth 17.

To that end, in some non-limiting embodiments of the present technology, the optimizing the initial force may comprise: (i) determining a set of admissible forces associated with the tooth 15; and (ii) selecting a respective valid force from the set of admissible forces such that it causes another maximum possible displacement of the tooth 3D representation 700 towards the aligned position provided that collisions thereof with tooth 3D representations associated with the first adjacent tooth 13 and the second adjacent tooth 17 are minimized.

How the set of admissible forces may be determined, in accordance with certain non-limiting embodiments of the present technology, will now be described.

Determining Admissible Force Range

In accordance with certain non-limiting embodiments of the present technology, the processor 550 may be configured to determine the set of admissible forces associated with the tooth 15 based on a range of admissible stress values predetermined therefor.

Referring back to FIGS. 3A and 3B, in the context of the present specification, the term "admissible stress value" denotes an amount of stress that may be applied to the tissues of the periodontium 30 of the tooth 15 such that the root portion 28 would displace at a distance that is equal or less than the length of the PDL space 38. According to certain non-limiting embodiments of the present technology, an amount of stress corresponding to an admissible stress value may thus not cause the damage to the tissues of the periodontium 30.

According to certain non-limiting embodiments of the present technology, the processor 550 may be configured to determine the range of admissible stress values based on a Stress Cumulative Distribution Function (SCDF). In some non-limiting embodiments of the present technology, the SCDF may be predetermined for each of the upper teeth 16, such as the tooth 15, empirically, based on analyzing deformation features of the periodontium 30 under various external forces. Further, in specific non-limiting embodiments of the present technology, the analyzing the deformation forces may include analyzing a finite element model of the tooth 15, which the processor 550 may be configured to generate based on the tooth 3D representation 700. Broadly speaking, in these embodiments, the SCDF may be configured to return a portion of a surface of the PDL 34, where stress is greater than an amount of stress of interest caused by a given external force. Thus, according to certain non-limiting embodiments of the present technology, the SCDF may be formalized by the following equation:

$$\text{SDCF}(F_i, s_i) = S_i(PDL), \quad (1)$$

where $F_i$ is an external force;
$s_i$ is a respective amount of stress caused by the external force $F_i$; and
$S_i(PDL)$ is a portion of the surface of the PDL 34 influenced by a greater amount of stress than $s_i$.

Figure 9:
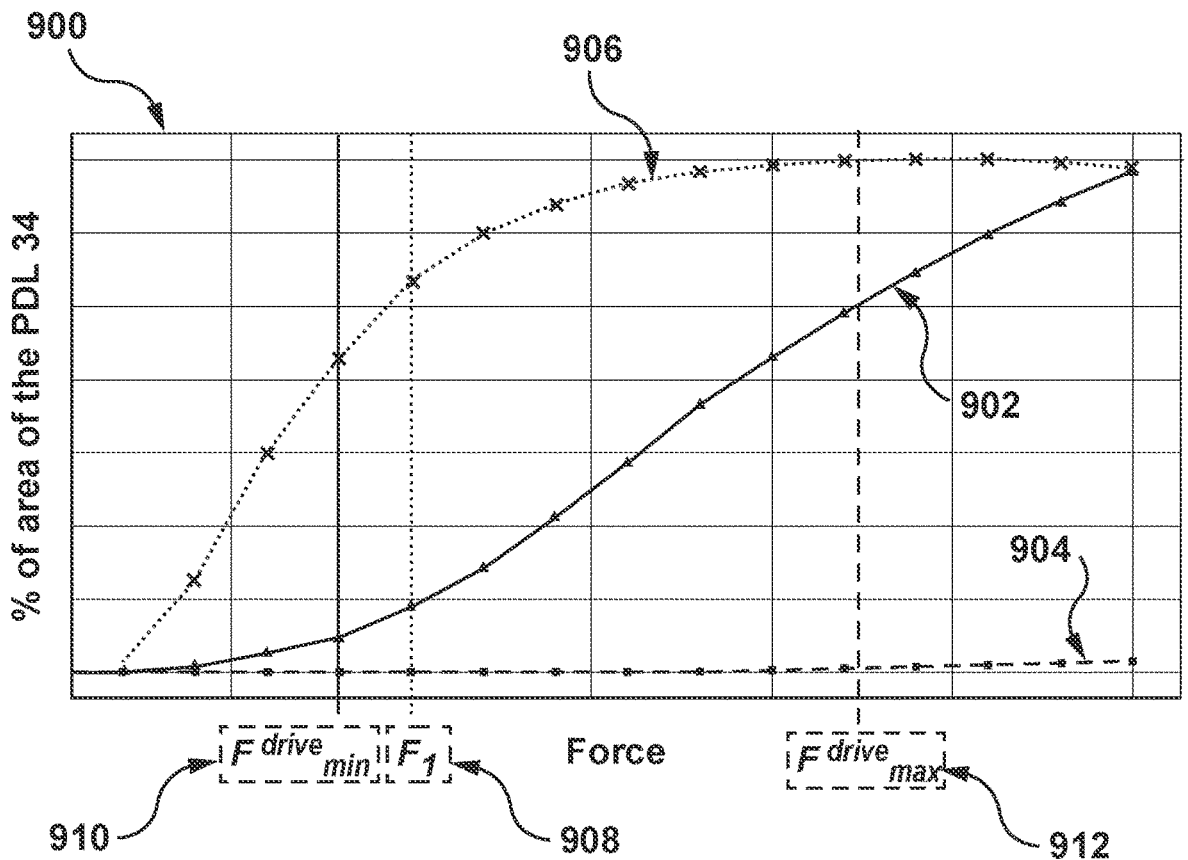
FIG. 9 depicts an example stress nephogram representative of a Stress Distribution Function applied, by the processor of FIG. 5, to determine admissible forces to be applied to the at least some of the subject's teeth of FIG. 1 to generate the respective trajectories therefor, in accordance with certain non-limiting embodiments of the present technology.

With reference to FIG. 9, there is provided a stress nephogram 900 having been generated, by the processor 550, for the tooth 15 based on analyzing the tooth 3D representation 700, in accordance with certain non-limiting embodiments of the present technology.

According to certain non-limiting embodiments of the present technology, the stress nephogram 900 is indicative of stress distribution within the PDL 34 under influence of various external forces defining the SCDF for the tooth 15. More specifically, the stress nephogram 900 shows a behaviour of stress distributed within a respective portion of the PDL 34 (indicated by the vertical axis in the stress nephogram 900) caused by a respective external force (indicated by the horizontal axis in the stress nephogram 900). Also, the stress nephogram 900 may include data indicative of strain distribution within the PDL 34 under respective external forces.

Thus, in certain non-limiting embodiments of the present technology, the stress nephogram 900 may include (1) an admissible stress distribution graph 902 indicating a distribution of admissible stress, which does not cause permanent damage to the PDL 34, and thus may cause the tooth 15 either to move or rest within the upper arch form 20; (2) a dangerous stress distribution graph 904 indicating a distribution of dangerous stress, which, when applied to the PDL 34, may cause permanent damage thereof; and (3) an admissible strain distribution graph 906 indicating distribution of admissible strain within the PDL 34.

For example, according to the stress nephogram 900, a given force 908, $F_1$, applied to the tooth 15 may cause an admissible amount of stress to, approximately, 9% of a surface of the PDL 34; an admissible amount strain to around 53% of the surface of the PDL 34, and no dangerous stress to the PDL 34. Thus, in this example, $\text{SDCF}(F_1, s_1) = 0$.

Thus, according to certain non-limiting embodiments of the present technology, the processor 550 may be configured to identify the set of admissible forces including: (i) a minimum drive force 910, $F^{drive}_{min}$, corresponding to a minimum amount of stress, $s^{min}$, applied to the PDL 34 causing the tooth 15 to move, and (ii) based on the dangerous stress distribution graph 904, a maximum drive force 912, $F^{drive}_{max}$, corresponding to an amount of stress beyond which the permanent damage to the PDL 34 may be caused, $s^{max}$. Thus, based on the stress nephogram 900, the processor 550 may be configured to identify the following sets of forces:

1) the set of admissible forces applicable to the PDL 34 without causing the permanent damage thereto:

$$F^{adm} : \text{SCDF}(F_i, s^{max}) \sim 0, \text{ further including:} \quad (2)$$

2) a set of forces causing the tooth 15 to rest:

$$F^{rest} : \text{SCDF}(F_i, s^{min}) \sim 0, \text{ and} \quad (3)$$

3) a set of drive forces causing the tooth 15 to move in a respective direction associated with each force therefrom:

$$F^{drive} : \begin{cases} SCDF(F_i, s^{max}) \sim 0 \\ SCDF(F_i, s^{min}) > 0 \end{cases} \Rightarrow F^{drive} \in [F_{min}^{drive}, F_{max}^{drive}]. \quad (4)$$

Accordingly, as it may become apparent from the above, any force beyond the set of admissible forces $F^{adm}$ may cause the permanent damage to the PDL 34 of the tooth 15.

Thus, the processor 550 may be configured to determine, based on a respective tooth 3D representation, a respective range of admissible forces for each modelled movement (such as translation, rotation, controlled/uncontrolled tipping, or extrusion/intrusion, for example) of each one of the upper teeth 16 for further determining a respective valid force therefrom.

As mentioned earlier, the processor 550 may be configured to use the set of admissible forces $F^{adm}$ to determine the respective valid force to be further applied to the tooth 15, in the course of the orthodontic treatment, thereby determining the given segment of the second trajectory 804.

Treatment Plan Optimization

As previously mentioned, according to certain non-limiting embodiments of the present technology, the processor 550 may be configured to determine the valid force to be applied to the tooth 15 by solving the following optimization problem: (1) minimizing the overall duration of the orthodontic treatment while (2) minimizing collisions of the tooth 15 with at least one of the first adjacent tooth 13 and the second adjacent tooth 17. In these embodiments, this optimization problem may be analytically defined by the following equation of a Loss function:

Loss=Goal+α·CollisionPenalty+
β·ForceBudjectPenalty,     (5)

where $$Goal = \max_j (t_j^{fin})$$

is a maximum time for a given tooth to reach a respective target position, such as $t^{fin}_2$ associated with the tooth 15;

CollisionPenalty is a term indicative of collisions between tooth 3D representations of a pair of adjacent teeth, such as those of the tooth 15 and one of the first adjacent tooth 13 and the second adjacent tooth 17;

ForceBudjectPenalty is a term indicative of feasibility of the orthodontic treatment in terms of admissibility of applied forces; and α and β are coefficient iteratively determined during the optimization process.

In some non-limiting embodiments of the present technology, the processor 550 may be configured to gradually increase the coefficients α and β until the reaching a global minimum of the Loss function.

According to certain non-limiting embodiments of the present technology, to implement the optimization process, thereby minimizing the Loss function, the processor 550 may be configured to apply at least one optimization algorithm. It should be noted that how the at least one optimization algorithm is implemented is not limited; however, in specific non-limiting embodiments of the present technology, the at least one optimization algorithm may include at least one of a gradient descent optimization algorithm and simulated annealing optimization algorithm, as an example.

In some non-limiting embodiments of the present technology, the ForceBudgetPenalty may be minimized by the processor 550 determining a given force to be applied within a given trajectory associated with a respective tooth (such as the second trajectory 804 of the tooth 15) based on a range of admissible stress values, that is by selecting the given force from the set of admissible forces $F^{adm}$, as described above in the respective section of the present specification.

How the CollisionPenalty may be defined and further minimized, according to certain non-limiting embodiments of the present technology, will be described below.

Collision Minimization

According to certain non-limiting embodiments of the present technology, when generating the given segment of the second trajectory 804 associated with the tooth 15, the processor 550 may be configured to determine if, within the given segment, the tooth 3D representation 700 collides with a tooth 3D representation of one of the first adjacent tooth 13 and the second adjacent tooth 17.

Figure 10:
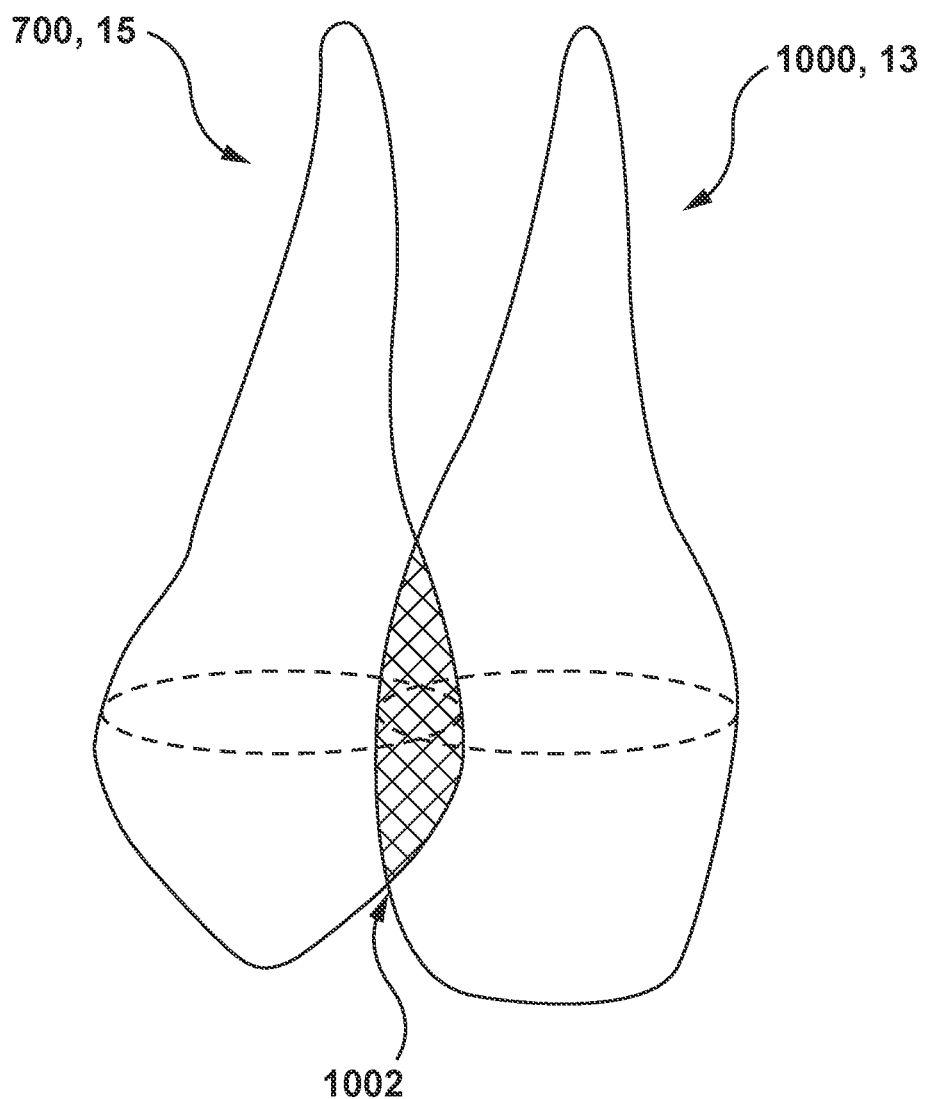
FIG. 10 depicts a schematic diagram of a collision between 3D models of a pair of adjacent ones of the subject's teeth of FIG. 1, in accordance with certain non-limiting embodiments of the present technology.

With reference to FIG. 10, there is depicted a schematic diagram of the tooth 3D representation 700 of the tooth 15 colliding with an adjacent tooth 3D representation 1000 of the first adjacent tooth 13, in accordance with certain non-limiting embodiments of the present technology. As can be appreciated, the collision between the tooth 3D representation 700 and the adjacent tooth 3D representation 1000 forms an overlap region 1002.

In accordance with certain non-limiting embodiments of the present technology, to determine presence (or, in other words, an occurrence) of the collision, the processor 550 may be configured to execute one or more collision detection algorithms. It should be expressly understood that implementation of the collision detection algorithms is not limited, and may include a mesh collision detection algorithm such as, without limitation: an axis-aligned bounding boxes collision detection algorithm, bounding volume hierarchy collision detection algorithm, and the like.

In specific non-limiting embodiments of the present technology, the processor 550 may be configured to apply a collision detection and prevention algorithm based on analyzing point clouds associated with each of the tooth 3D representation 700 and the adjacent tooth 3D representation 1000 as described in a co-owned U.S. patent application Ser. No. 16/703,424 entitled "SYSTEMS AND METHODS FOR DETERMINING ORTHODONTIC TREATMENTS", and filed on Dec. 4, 2019; the content of which is hereby incorporated by reference in its entirety.

In other specific non-limiting embodiments of the present technology, the processor 550 may be configured to detect the collision between the tooth 3D representation 700 and the adjacent tooth 3D representation 1000 by analyzing depth map images thereof. In these embodiments, the processor 550 may be configured to analyze movements of the adjacent tooth 3D representation 1000 within a coordinate system (not depicted) associated with the tooth 3D representation 700 in order to detect any intersection thereof in the course of their movements along the first trajectory 802 and the second trajectory 804 respectively associated therewith.

Thus, according to certain non-limiting embodiments of the present technology, by applying the one or more collision detection algorithms, the processor 550 may be configured to determine, for the given segment of the plurality of segments associated with the second trajectory 804: (1) a moment in time when the tooth 3D representation 700 collides with the adjacent tooth 3D representation 1000, $t^{collision}$; and (2) a moment in time, at which the tooth 3D representation 700 has gone through the adjacent tooth 3D representation 1000 and decoupled therefrom, $t^{decoupling}$. Further, the processor 550 may be configured to detect the collision by analyzing if the respective predetermined treatment interval associated with the given segment $<t^i, t^{i+1}>$ intersects with a time interval associated with the collision $<t^{collision}, t^{decoupling}>$. Thus, in response to detecting an intersection between the respective predetermined treatment interval and the time interval associated with the collision, the processor 550 may be configured to determine the occurrence of the collision on the given segment of the second trajectory 804.

Further, according to certain non-limiting embodiments of the present technology, the processor 550 may be configured to numerically determine an extent of the collision between the tooth 3D representation 700 and the adjacent tooth 3D representation 1000 to be minimized as CollisionPenalty of the Loss function defined by Equation (5).

In some non-limiting embodiments of the present technology, a maximum volume of the overlap region 1002 between the tooth 3D representation 700 and the adjacent tooth 3D representation 1000 may be indicative of the extent of the collision. Thus, in these embodiments, the CollisionPenalty of Equation (5) may be formalized as follows:

$$CollisionPenalty = \sum_{j \neq j+1} \left( \max_{t_i} (\text{Intersection}(G_j(X_j(t^i)), G_{j+1}(X_{j+1}(t^i)))) \right), \quad (6)$$

where $G_j(X_j(t^i))$ is a surface of a given tooth 3D representation (such as the tooth 3D representation 700 of the tooth 15) associated with its current position, within the coordinate system 650, $X_j$ at a given moment in a given moment time $t^i$;

$G_{j+1}(X_{j+1}(t^i))$ is a surface of an adjacent tooth 3D representation (such as the adjacent tooth 3D representation 1000 of the first adjacent tooth 13) associated with its current position, within the coordinate system 650, $X_{j+1}$ at the given moment in time $t^i$.

Certain non-limiting embodiments of the present technology have been developed based on a developers' appreciation that translational movements of the tooth 3D representation 700 may be associated with a higher efficiency of the orthodontic treatment. Thus, in these embodiments, the processor 550 may be configured to minimize the CollisionPenalty by generating intermediate trajectory points (such as the at least one intermediate trajectory point 808 of FIG. 8) to generate respective linear segments of the second trajectory 804.

Figure 11:
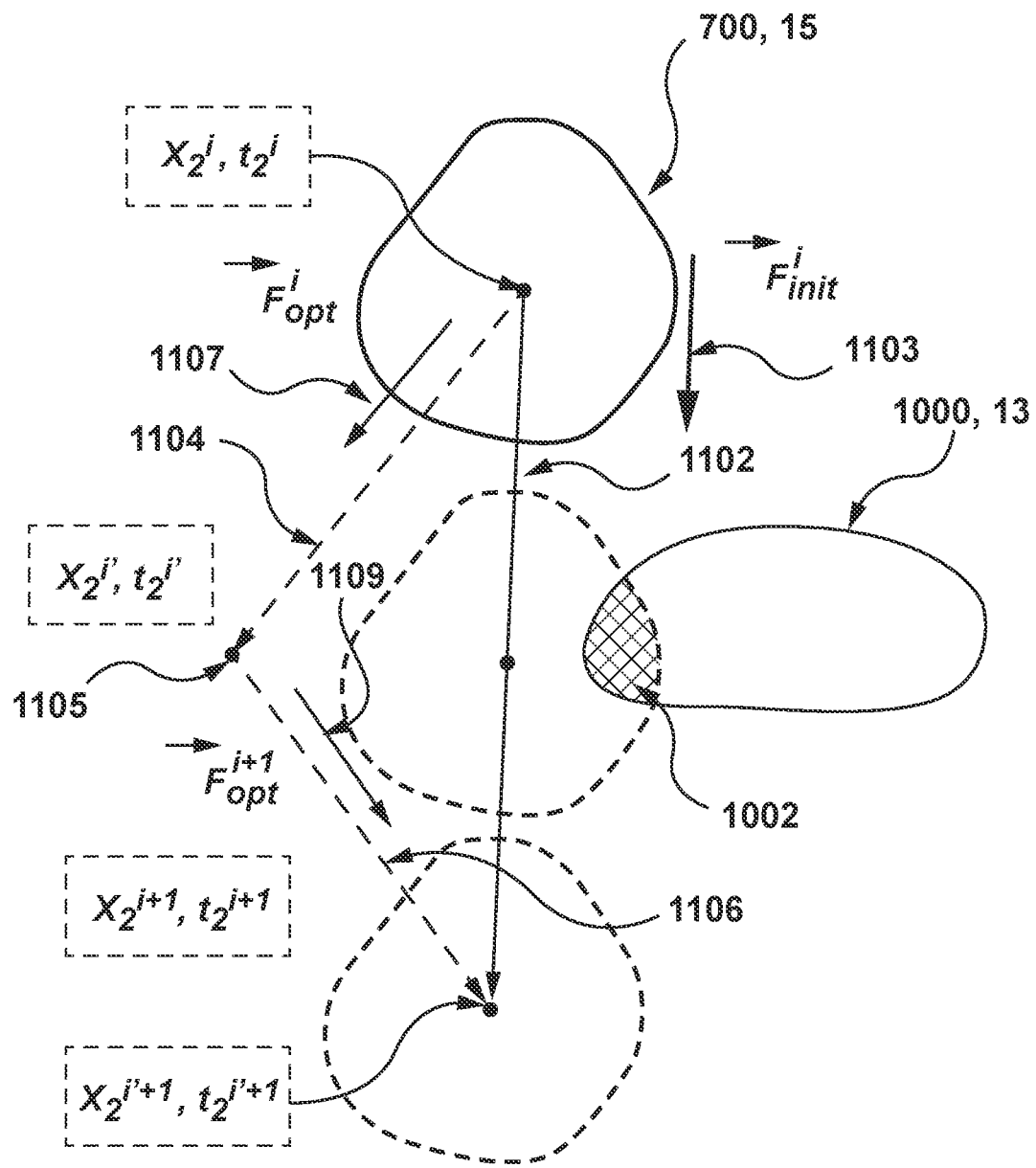
FIG. 11 depicts a schematic diagram for a process of minimizing, by the processor of FIG. 5, the collision of FIG. 10 identifying an intermediate trajectory point for at least one of the 3D models of the pair of adjacent ones of the subject's teeth of FIG. 1, in accordance with certain non-limiting embodiments of the present technology.

With reference to FIG. 11, there is depicted a top view of the tooth 3D representation 700 and the adjacent tooth 3D representation 1000 for illustrating a process for generating, by the processor 550, a given intermediate trajectory point 1105 for the second trajectory 804, in accordance with certain non-limiting embodiments of the present technology.

Let it be assumed, that under an initial force 1103, $F_{init}^i$, applied by the processor 550, the tooth 3D representation 700 is to move along an initial path 1102 from a start position $X_2^i$ to an end position $X_2^{i+1}$ in an initial predetermined treatment interval $<t^i, t^{i+1}>$. As mentioned earlier in respect of Equations (2) to (4), in some non-limiting embodiments of the present technology, the processor 550 may have been configured to determine the initial force 1103 based on the set of admissible forces to cause an initial maximum displacement of the tooth 3D representation 700, thereby defining the end position thereof $X_2^{i+1}$. However, as it can be appreciated, on the initial path 1102, the tooth 3D representation 700 may collide with the adjacent tooth 3D representation 1000, thereby forming, for example, the overlap region 1002.

In this regard, as described above, the processor 550 may be configured to minimize the volume of the overlap region 1002 (which is indicative of the CollisionPenalty in the present non-limiting example), thereby identifying the given intermediate trajectory point 1105. Thus, according to certain non-limiting embodiments of the present technology, minimizing the CollisionPenalty, the processor 550 may be configured to optimize the initial force 1103.

According to certain non-limiting embodiments of the present technology, to optimize the initial force 1103, the processor 550 may be configured to modulate a magnitude and a direction thereof, based on the set of admissible forces $F^{adm}$, thereby determining therefrom a first optimized force 1107, $F_{opt}^i$, causing the tooth 3D representation 700 to deviate from the initial path 1102 towards the given intermediate trajectory point 1105, thereby avoiding the collision with the adjacent tooth 3D representation 1000. Further, the processor 550 may be configured to determine a second optimized force 1109, $F_{opt}^{i+1}$, causing the tooth 3D representation 700 to move from the given intermediate point $X_2^{i'}$ to the target end position $X_2^{i+1}$.

In some non-limiting embodiments of the present technology, the processor 550 may be configured to determine the first optimized force 1107 and the second optimized force 1109, iteratively selecting forces from the set of admissible forces $F^{adm}$ causing a minimum deviation of the tooth 3D representation 700 from the initial path 1102. In other words, the processor 550 may be configured to identify the given intermediate trajectory point 1105 to be associated with a given intermediate moment in time $t_2^{i'}$ such that a first predetermined treatment interval $<t^i, t^{i'}>$ and a second predetermined treatment interval $<t^{i'}, t^{i+1}>$ are minimized by the Loss function.

By doing so, based on the given intermediate trajectory point 1105, the processor 550 may be configured to cause the tooth 3D representation 700 to move to the end position $X_2^{i+1}$ along a first adjusted path 1104 and a second adjusted path 1106. Accordingly, the first adjusted path 1104 may be said to define a first maximum displacement of the tooth 3D representation 700, in the first predetermined treatment interval $<t^i, t^{i'}>$, from the start position $X_2^i$ towards an intermediate position thereof $X_2^{i'}$ defined by the given intermediate trajectory point 1105; and the second adjusted path 1106 may be said to define a second maximum displacement of the tooth 3D representation 700, in the second predetermined treatment interval $<t^{i'}, t^{i+1}>$, from the intermediate position XY towards the end position thereof $X_2^{i+1}$. In other words, the processor 550 may thus be configured to cause the tooth 3D representation 700 to move towards the target position thereof $X_2^{i+1}$ over a minimized amount of time avoiding collisions with the adjacent tooth 3D representation 1000.

Thus, the first adjusted path 1104 and the second adjusted path 1106 may be used by the processor 550 to form respective ones of the plurality of segments of the second trajectory 804 for the tooth 15, whereby the first optimized force 1107 and the second optimized force 1109 may be considered valid forces.

As it may become apparent, in those non-limiting embodiments of the present technology, where the tooth 3D representation 700 does not collide with the adjacent tooth 3D representation 1000 on the initial path 1102, the processor may be configured to define the initial force 1103 as being the valid force.

Further, considering movements of the tooth 3D representation 70) and the adjacent tooth 3D representation 1000 in an aggregate manner, for example in case of simultaneous movement thereof, for effective collision resolution, according to certain non-limiting embodiments of the present technology, the processor 550 may be configured to pre-define priority rules for the movements of the tooth 3D representation 700 and the adjacent tooth 3D representation 1000 within the 3D model 600. For example, in some non-limiting embodiments of the present technology, the processor 550 may be configured to allow movement of that one of the tooth 3D representation 700 and the adjacent tooth 3D representation 1000, which started its movement first, and at the same time, suspend movement of the other one of the tooth 3D representation 700 and the adjacent tooth 3D representation 1000. In some non-limiting embodiments of the present technology, the suspension of a respective movement may be implemented by applying, by a processor 550, a zero vector to a respective optimized force applied to a given one of the tooth 3D representation 700 and the adjacent tooth 3D representation 1000, as will be described below.

Also, as it will become apparent from the description provided below, in other non-limiting embodiments of the present technology, the initial force 1103 may cause respective collisions among at least some tooth 3D representations of other ones of the upper teeth 16. Accordingly, in these embodiments, in accordance with Equation (6), the CollisionPenalty may be indicative of a sum of extents of the respective collisions. In this regard, by minimizing the CollisionPenalty, thereby optimizing the initial force 1103, the processor 550 may be configured to determine, based on the set of admissible forces $F^{adm}$ as described above, the first optimized force 1107 and the second optimized force 1109 not causing the respective collisions of the tooth 3D representations of the other ones of the upper teeth 16. Therefore, by applying newly optimized the first optimized force 1107 and the second optimized force 1109, the processor 550 may be configured to cause the tooth 3D representation 700 to perform, respectively, a third maximum displacement and a fourth maximum displacement (both not depicted), thereby re-determining the first adjusted path 1104 and the second adjusted path 1106.

Accordingly, the processor 550 may further be configured to apply the above-described priority rules to the respective ones of the tooth 3D representations of the other ones of the upper teeth 16.

Thus, by applying the approach described hereinabove, the processor 550 may be configured to determine each segments of the plurality of segments associated with the second trajectory 804, along each of which the tooth 3D representation 700 associated with the tooth 15 would move, within the 3D model 600, under a respective valid force causing a respective maximum displacement thereof, in a respective one of the plurality of predetermined treatment intervals, towards the aligned position provided that collisions among the at least some of tooth 3D representations including the tooth 3D representation 700 are minimized. The second trajectory 804 may thus be used for planning the orthodontic treatment.

Treatment Plan Determination

As noted hereinabove, a displacement of a given tooth 3D representation caused by a respective valid force, such as the first maximum displacement of the tooth 3D representation 700 under the first optimized force 1107, may cause application of additional forces to at least some of tooth 3D representations of other ones of the upper teeth 16 (such as those involved in the orthodontic treatment). Thus, for planning the orthodontic treatment for a respective treatment interval (such as the first treatment interval mentioned above) using the aligner 10, the processor 550 may be configured to determine the additional forces and, if necessary, further determine additional constraints (aside from the above-described safety requirements) therefor, due to, for example, suspension of movement of a respective tooth 3D representation or unnecessity of movement thereof, within a respective segment of the second trajectory 804, altogether.

According to certain non-limiting embodiments of the present technology, to determine the additional forces, the processor 550 may be configured to apply a Displacement Response Force Distribution Function (DRFDF). According to certain non-limiting embodiments of the present technology, the DRFDF may be constructed based on a superposition property of the forces caused by a displacement of a given tooth 3D representation within the 3D model 600. Thus, for example, the additional forces caused by the application of the first optimized force 1107 applied to the tooth 3D representation 700 may be determined in accordance with the following equation:

$$F_{1\ldots n} = DRFDF_1 \times \vec{d}_1, \quad (7)$$

where $F_{1\ldots n}$ is a vector of the additional forces applied, in the respective predetermined treatment interval, to respective tooth 3D representations involved in the orthodontic treatment in response to applying the first optimized force 1107 causing the first maximum displacement of the tooth 3D representation 700 $\vec{d}_1$; and $DRFDF_1$ is a matrix of coefficients indicative of force magnitude values of the additional forces associated with the applying the first optimized force 1107.

According to certain non-limiting embodiments of the present technology, the $DRFDF_1$ may have dimensions of (6n×6), where n is a number of the respective tooth 3D representations involved in the orthodontic treatment using the aligner 10, and the dimension 6 corresponds to 6 DOF of each of the respective tooth 3D representations, along which a respective one of the additional forces propagates.

According to certain non-limiting embodiments of the present technology, the $DRFDF_1$ may be populated, for example, based on finite element analysis of the respective tooth 3D representations, their associated PDLs (such as the PDL 34 associated with the tooth 3D representation 700 of the tooth 15) with respective configurations of the aligner 10 applied thereto.

Accordingly, in additional non-limiting embodiments of the present technology, where the additional forces are caused by respective displacements of more than one tooth 3D representations within the 3D model 600, the processor 550 may be configured to determine them in accordance with the following equation:

$$F_{1\ldots n} = \Sigma_j (DRFDF_j \times \vec{d}_j). \quad (8)$$

Thus, based on the applying the DRFDF, the processor 550 may be configured to determine the additional forces $F_{1\ldots n}$ including their magnitudes and directions satisfying the following constraints as described above in above in respect of Equations (2) to (4):

$F_j \in F_j^{adm}$—an admissible stress constraint;

$F_j \in F_j^{drive}$—forces used to cause a given tooth 3D representation to move in directions associated therewith; and $F_j \in F_j^{rest}$—forces used to cause the given tooth 3D representation to rest.

It should be expressly understood that the above list of constraints applied to the additional forces $F_{1\ldots n}$ is not exhaustive, and in additional non-limiting embodiments of the present technology, may further include constraints for a respective lower boundary of each of the additional forces $F_{1\ldots n}$—for example, to be corresponding to a boundary of a respective set of forces causing a given tooth to rest, $F_j^{rest}$. Such constraints may be used to allow for proper reformation of a PDL of a respective one of the upper teeth 16.

Thus, according to certain non-limiting embodiments of the present technology, based on the DRFDF as defined by Equations (7) and (8), the processor 550 may be configured to determine each displacement of the respective tooth 3D representations within the 3D model 600, in the first predetermined treatment interval, caused by the additional forces applied thereto in response to, at least, the first maximum displacement of the tooth 3D representation 700 under the first optimized force 1107.

In some non-limiting embodiments of the present technology, by applying the approach described immediately above, the processor 550 may be further configured to determine maximum displacements of the respective tooth 3D representations of those of upper teeth 16 involved in the orthodontic treatment within other ones of the plurality of predetermined treatment intervals, thereby determining respective trajectories (such as at least the first trajectory 802 associated with the first adjacent tooth 13 and the third trajectory 806 associated with the second adjacent tooth 17) to be used for planning the orthodontic treatment.

Needless to say that, in additional non-limiting embodiments of the present technology, the processor 550 may be configured to apply the same approaches as described above, mutatis mutandis, to at least some of the lower teeth 27 for generating respective trajectories associated therewith to be used for planning the orthodontic treatment of the subject.

Thus, in some non-limiting embodiments of the present technology, the processor 550 may be configured to represent the orthodontic treatment in a form of a schedule defining movements of each of the upper teeth 16 in respective ones of the plurality of predetermined treatment intervals.

Figure 12:
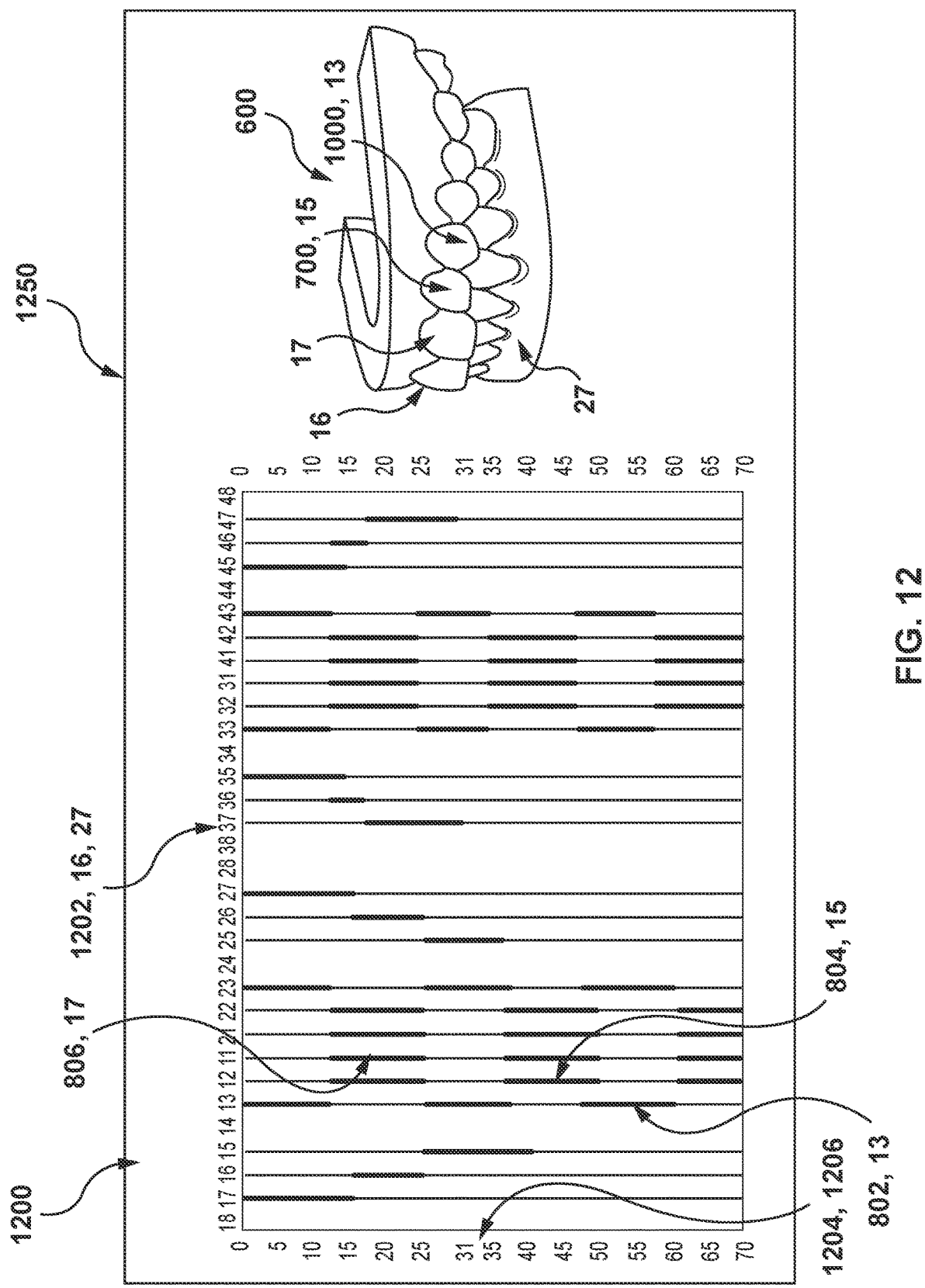
FIG. 12 depicts a schematic diagram of an example schedule representing trajectories determined, by the processor of FIG. 8, for the at least some of the subject's teeth present in FIG. 1 used for planning the orthodontic treatment for the subject, in accordance with certain non-limiting embodiments of the present technology.

With reference to FIG. 12, there is depicted a planned schedule 1200 of the orthodontic treatment, in accordance with certain non-limiting embodiments of the present technology.

In the depicted embodiments of FIG. 12, the planned schedule 1200 includes a horizontal axis 1202 representative of respective ordinal numbers of the upper teeth 16 and the lower teeth 27; and a vertical axis 1204 representative of a plurality of predetermined treatment intervals 1206 of the orthodontic treatment. Accordingly, each one of the upper teeth 16 and the lower teeth 27 may thus be associated with a respective trajectory defining movements thereof along an associated plurality of segments, within respective ones of the plurality of predetermined treatment intervals.

In some non-limiting embodiments of the present technology, each of the predetermined treatment intervals 1206 may be associated with using a respective configuration of the aligner 10 configured to apply, during a respective one of the plurality of predetermined treatment intervals 1206, respective so determined valid forces onto at least one of the upper teeth 16 and the lower teeth 27 causing them to move along respective segments of their associated trajectories. In some non-limiting embodiments of the present technology, each one of the plurality of predetermined treatment intervals 1206 may be equal and comprise, for example, 14 days. However, in other non-limiting embodiments of the present technology, based on specifics of a particular orthodontic treatment, the plurality of predetermined treatment intervals 1206 may include predetermined treatment intervals of various durations which may be less than or more than 14 days.

In some non-limiting embodiments of the present technology, the planned schedule 1200 may be displayed as a graphical user interface 1250 on the screen 422 of the system 400. The planned schedule 1200 may thus assist the clinician to monitor the so planned orthodontic treatment and allow modification thereof. In these embodiments, the graphical user interface 1250 may include the planned schedule 1200 and the 3D model 600 representing tooth positions of the upper teeth 16 and the lower teeth 27 at various ones of the plurality of predetermined treatment intervals 1206 in the course of the orthodontic treatment. In the depicted example of FIG. 12, the 3D model 600 is representative of the tooth 15 having reached the aligned position within the upper teeth 16 as a result of the planned orthodontic treatment.

However, in other non-limiting embodiments of the present technology, the planned schedule 1200 may not be displayed and may be stored in a form of program instructions, for example, in the solid-state drive 560, accessible by the processor 550 for retrieving data for executing the so planned orthodontic treatment.

Further, in some non-limiting embodiments of the present technology, upon acquiring data indicative of modification of at least one trajectory of trajectories of the planned schedule 1200, the processor 550 may be configured to re-generate at least some trajectories thereof considering the configuration of the at least one trajectory as a constant. In some non-limiting embodiments of the present technology, the modification may include, for example, modification of a given valid force associated with the given segment, thereby modifying its associated length or direction.

For example, the processor 550 may be configured to acquire data indicative of modification of the second trajectory 804. It is not limited how the processor 550 may acquire the data indicative of the modification of the second trajectory 804; and in some non-limiting embodiments of the present technology, the processor 550 may be configured to acquire the data indicative of the modification of the second trajectory 804 from the clinician, for example, via the user interface generated based on the planned schedule 1200. In other non-limiting embodiments of the present technology, the processor 550 may be configured to apply the modification to the given segment of the second trajectory 804 based on previous orthodontic treatments generated for a group of subjects.

In some non-limiting embodiments of the present technology, the modification of the second trajectory 804 may cause, for example, collisions along at least one of the first trajectory 802 and the third trajectory 806 respectively associated with the first adjacent tooth 13 and the second adjacent tooth 17. In other non-limiting embodiments of the present technology, the modification of the second trajectory 804 may cause application of forces associated with certain segments of at least one of the first trajectory 802 and the third trajectory 806, which are beyond respective sets of admissible forces.

Thus, in some non-limiting embodiments of the present technology, the processor 550 may be configured to re-generate at least one of the first trajectory 802 and the third trajectory 806 to meet the requirements in respect of the applied forces and minimize the collisions without modifying the second trajectory 804.

Figure 13:
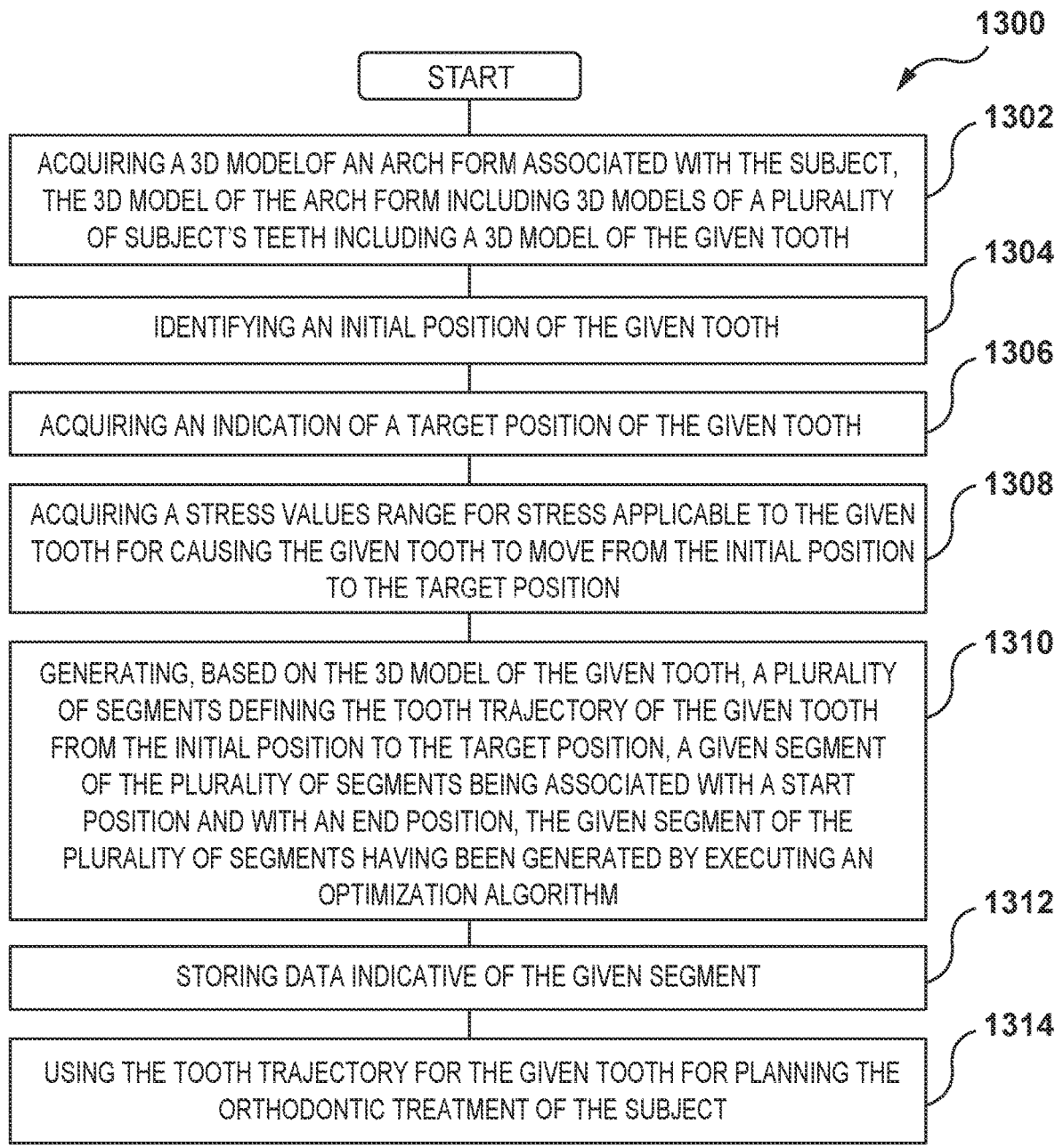
FIG. 13 depicts a flowchart of a method for planning the orthodontic treatment based on determining the respective trajectories for the at least some of the subject's teeth of FIG. 1, in accordance with certain embodiments of the present technology.

Given the architecture and the examples provided hereinabove, it is possible to execute a method for determining a tooth trajectory for a given one of subject's teeth (such as the tooth 15 of the upper teeth 16) defining movements thereof during an orthodontic treatment. With reference to FIG. 13, there is depicted a flowchart of a method 1300, according to certain non-limiting embodiments of the present technology. The method 1300 can be executed by a processor of a computing environment, such as the processor 550 of the computing environment 540.

Step 1302: Acquiring a 3D Model of an Arch Form Associated with the Subject, the 3D Model of the Arch Form Including 3D Models of a Plurality of Subject's Teeth Including a 3D Model of the Given Tooth The method 1300 commences at step 1302 with the processor 550 acquiring image data associated with the subject. For example, in certain non-limiting embodiments of the present technology, using the imaging device 430, the processor 550 may be configured to generate the 3D model 600 representative of the upper arch form 20 and the lower arch form 21 of the subject, as described above with reference to FIG. 6.

Further, according to some non-limiting embodiments of the present technology, the processor 550 may be configured to generate, based on the 3D model 600, respective tooth 3D representations, for example, of the upper teeth 16—such as the tooth 3D representation 700 of the tooth 15. The processor 550 may be further configured to use the tooth 3D representation 700 for determining a trajectory for the tooth 15 in the course of the orthodontic treatment—such as the second trajectory 804, as described above with reference to FIG. 8.

The method 1300 hence advances to step 1304.

Step 1304: Identifying an Initial Position of the Given Tooth

At step 1304, based on the tooth 3D representation 700, the processor 550 may be configured to identify an initial position of the tooth 15 within the upper arch form 20. To that end, according to certain non-limiting embodiments of the present technology, the processor may be configured 6 DOF of the tooth 3D representation 700 at the initial moment in time, $\langle X_2^{init}, t_2^{init} \rangle$, as described above with reference to FIG. 8.

Step 1306: Acquiring an Indication of a Target Position of the Given Tooth

At step 1306, the processor may be configured to acquire 6 DOF of the tooth 3D representation 700 associated with the target position for the tooth 15, $X_2^{fin}$. According to certain non-limiting embodiments of the present technology, the target position $X_2^{fin}$ may be associated with the aligned position of the tooth 15 within the upper arch form 20.

In some non-limiting embodiments of the present technology, the target position for the tooth 15 may be provided by the clinician. In other non-limiting embodiments of the present technology, the processor 550 may be configured to determine the target position based on averaged data associated with aligned teeth received from a group of subjects.

The method 1300 thus proceeds to step 1308.

Step 1308: Acquiring a Stress Values Range for Stress Applicable to the Given Tooth for Causing the Given Tooth to Move from the Initial Position to the Target Position According to certain non-limiting embodiments of the present technology, at step 1308, the processor 550 may be configured to determine a set of admissible forces $F^{adm}$ to be applied to the tooth 3D representation 700 to generate respective segments of the plurality of segments associated with the second trajectory 804.

According to certain non-limiting embodiments of the present technology, the set of admissible forces $F^{adm}$ may be determined based on the range of admissible stress values associated with the tooth 15, which, when applied to the periodontium 30, may not cause the damage thereof.

In some non-limiting embodiments of the present technology, the range of the admissible stress values may be determined based on the SDF as described above with reference to FIG. 9.

The method 1300 thus proceeds to step 1310.

Step 1310: Generating, Based on the 3D Model of the Given Tooth, a Plurality of Segments Defining the Tooth Trajectory of the Given Tooth from the Initial Position to the Target Position, a Given Segment of the Plurality of Segments being Associated with a Start Position and with an End Position, the Given Segment of the Plurality of Segments Having been Generated by Executing an Optimization Algorithm At step 1310, according to certain non-limiting embodiments of the present technology, the processor 550 may be configured to generate a given segment associated with the second trajectory 804.

To that end, as described above, with reference to FIG. 11, first, the processor 550 may be configured to apply the initial force 1103 to the tooth 3D representation 700. Accordingly, the application of the initial force 1103 may cause the tooth 3D representation 700 to move from the start position $X_2^i$ associated with the given segment towards the end position $X_2^{i+1}$, thereby defining the initial path 1102 for the tooth 3D representation 700. According to certain non-limiting embodiments of the present technology, the processor 550 may be configured to determine the initial force 1103 to cause an initial maximum displacement of the tooth 3D representation 700.

However, as noted above, according to certain non-limiting embodiments of the present technology, the processor 550 may be configured to determine the initial force 1103 to violate certain constraints. For example, the initial force 1103 may have the magnitude and the direction such that, when applied to the tooth 15, the initial force may cause the damage to the tissues of the periodontium 30. In another example, the initial force 1103 may cause collisions of the tooth 3D representation 700 with tooth 3D representations corresponding to teeth adjacent to the tooth 15—such as the adjacent tooth 3D representation 1000 of the first adjacent tooth 13. In the example, the collision may be represented by the overlap region 1002, as described above with reference to FIGS. 10 and 11.

In some non-limiting embodiments of the present technology, the processor 550 may be configured to determine the occurrence of the collision between the tooth 3D representation 700 and the adjacent tooth 3D representation 1000 based on one of the collision detection algorithms described above.

Thus, according to certain non-limiting embodiments of the present technology, the processor 550 may be configured to construct a loss function, such as the Loss defined by Equation (5), and apply an optimization algorithm to minimize it, thereby modulating the magnitude and the direction of the initial force 1103 to determine the first optimized force 1107. In some non-limiting embodiments of the present technology, the optimization algorithm may include at least one of a gradient descent optimization algorithm and simulated annealing optimization algorithm.

Accordingly, by applying the optimization algorithm, the processor 550 may be configured to determine the first optimized force 1107 by iteratively selecting forces from the set of admissible forces $F^{adm}$ causing a minimum deviation of the tooth 3D representation 700 from the initial path 1102, thereby minimizing the extent (that is the overlap region 1002) of the collision between the tooth 3D representation 700 and the adjacent tooth 3D representation 1000. Thus, the processor 550 may be configured to identify the given intermediate trajectory point 1105. In other words, the processor 550 may be configured to identify the given intermediate trajectory point 1105 to be associated with a given intermediate moment in time $t_2^{i'}$ such that the first predetermined treatment interval $<t^i, t^{i'}>$ and the second predetermined treatment interval $<t^{i'}, t^{i'+1}>$ are minimized by the Loss function. Further, the processor 550 may be configured to determine the second optimized force 1109 causing the tooth 3D representation 700 to move from the given intermediate point $X_2^{i'}$ to the target end position $X_2^{i+1}$ during the second predetermined treatment interval $<t^{i'}, t^{i'+1}>$.

By doing so, based on the given intermediate trajectory point 1105, the processor 550 may be configured to cause the tooth 3D representation 700 to move to the end position $X_2^{i+1}$ along the first adjusted path 1104 and the second adjusted path 1106. Accordingly, the first adjusted path 1104 may be said to define a first maximum displacement of the tooth 3D representation 700, in the first predetermined treatment interval $<t^i, t^{i'}>$, from the start position $X_2^i$ towards an intermediate position thereof $X_2^{i'}$ defined by the given intermediate trajectory point 1105; and the second adjusted path 1106 may be said to define a second maximum displacement of the tooth 3D representation 700, in the second predetermined treatment interval $<t^{i'}, t^{i'+1}>$, from the intermediate position $X_2^{i'}$ towards the end position thereof $X_2^{i+1}$. In other words, the processor 550 may thus be configured to cause the tooth 3D representation 700 to move towards the target position thereof $X_2^{i+1}$ over a minimized amount of time avoiding collisions with the adjacent tooth 3D representation 1000.

Thus, the first adjusted path 1104 and the second adjusted path 1106, determined by applying the optimization algorithm, may be used by the processor 550 to form respective ones of the plurality of segments of the second trajectory 804 for the tooth 15, whereby the first optimized force 1107 and the second optimized force 1109 may be considered valid forces.

In some non-limiting embodiments of the present technology, at least one of the first adjusted path 1104 and the second adjusted path is linear.

Also, as mentioned hereinabove, in other non-limiting embodiments of the present technology, the initial force 1103 may cause respective collisions among at least some tooth 3D representations of other ones of the upper teeth 16. Accordingly, in these embodiments, in accordance with Equation (6), the CollisionPenalty may be indicative of a sum of extents of the respective collisions. In this regard, by minimizing the Collisio1Penalty, thereby optimizing the initial force 1103, the processor 550 may be configured to determine, based on the set of admissible forces $F^{adm}$ as described above, the first optimized force 1107 and the second optimized force 1109 not causing the respective collisions of the tooth 3D representations of the other ones of the upper teeth 16. Therefore, by applying newly optimized the first optimized force 1107 and the second optimized force 1109, the processor 550 may be configured to cause the tooth 3D representation 700 to perform, respectively, a third maximum displacement and a fourth maximum displacement (both not depicted), thereby re-determining the first adjusted path 1104 and the second adjusted path 1106.

As it may become apparent, in those non-limiting embodiments of the present technology, where the initial force 1103 does not violate the above-identified constraints (not depicted), it may be determined, by the processor 550, as being the valid force.

Further, according to certain non-limiting embodiments of the present technology, by applying the approach described hereinabove, the processor 550 may be configured to determine each segments of the plurality of segments associated with the second trajectory 804, along each of which the tooth 3D representation 700 associated with the tooth 15 would move, within the 3D model 600, under a respective valid force causing a respective maximum displacement thereof, in a respective one of the plurality of predetermined treatment intervals, towards the aligned position provided that collisions among the at least some of tooth 3D representations including the tooth 3D representation 700 are minimized. The second trajectory 804 may thus be used for planning the orthodontic treatment.

The method hence advances to step 1312

Step 1312: Storing Data Indicative of the Given Segment

At step 1312, according to certain non-limiting embodiments of the present technology, the processor 550 may be configured to store, for example, in the solid-state drive 560, data indicative of each one of the plurality of segments associated with the second trajectory 804 for further planning the orthodontic treatment.

The method thus proceeds to step 1314.

Step 1314: Using the Tooth Trajectory for the Given Tooth for Planning the Orthodontic Treatment of the Subject According to certain non-limiting embodiments of the present technology, the processor 550, based on the DRFDF as defined above by Equations (7) and (8), may be configured to determine the additional forces applied to other tooth 3D representations of the upper teeth 16 involved in the orthodontic treatment, application of which is caused, for example, by the first maximum displacement of the tooth 3D representation 700.

By so doing, according to certain non-limiting embodiments of the present technology, based on the DRFDF, the processor 550 may be configured to determine each displacement of the respective tooth 3D representations within the 3D model 600, in the first predetermined treatment interval, caused by the additional forces applied thereto in response to, at least, the first maximum displacement of the tooth 3D representation 700 under the first optimized force 1107.

In some non-limiting embodiments of the present technology, by applying the approach described immediately above, the processor 550 may be further configured to determine maximum displacements of the respective tooth 3D representations of those of upper teeth 16 involved in the orthodontic treatment within other ones of the plurality of predetermined treatment intervals, thereby determining respective trajectories (such as at least the first trajectory 802 associated with the first adjacent tooth 13 and the third trajectory 806 associated with the second adjacent tooth 17) to be used for planning the orthodontic treatment.

According to certain non-limiting embodiments of the present technology, for planning the orthodontic treatment, the processor 550 may be configured to represent the so determine trajectories (such as the first trajectory 802, the second trajectory 804, and the third trajectory 806) in a form of a schedule, such as the planned schedule 1200 depicted in FIG. 12. In this regard, the planned schedule 1200 is representative of each one of the upper teeth 16 and the lower teeth 27 being associated with a respective trajectory defining movements thereof along an associated plurality of segments, within respective ones of the plurality of predetermined treatment intervals 1206.

In some non-limiting embodiments of the present technology, each of the predetermined treatment intervals 1206 may be associated with using a respective configuration of the aligner 10 configured to apply, during a respective one of the plurality of predetermined treatment intervals 1206, respective so determined valid forces onto at least one of the upper teeth 16 and the lower teeth 27 causing them to move along respective segments of their associated trajectories.

In some non-limiting embodiments of the present technology, each one of the plurality of predetermined treatment intervals 1206 may be equal and comprise, for example, 14 days. However, in other non-limiting embodiments of the present technology, based on specifics of a particular orthodontic treatment, the plurality of predetermined treatment intervals 1206 may include predetermined treatment intervals of various durations which may be less than or more than 14 days.

Thus, certain embodiments of the method 1300 allow developing more efficient and safer orthodontic treatments. More specifically, applying the method 1300 for planning the orthodontic treatment may allow (1) avoiding application of forces that may cause damage to tissues of periodontium associated with respective ones of the subject's teeth; (2) minimizing extents of collisions among the respective ones of subject's teeth; while (3) maximizing displacements of each of the respective ones of the subject's teeth, thereby reducing a number of associated aligners to be used in the course of the planned orthodontic treatment.

The method 1300 hence terminates.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for determining a tooth trajectory for a given tooth of a subject, the tooth trajectory defining movements of the given tooth during an orthodontic treatment, the method being executable by a processor of an electronic device, the method comprising:
   acquiring a 3D model of an arch form associated with the subject, the 3D model of the arch form including 3D models of a plurality of subject's teeth including a 3D model of the given tooth, the 3D model being based on image data acquired by an intraoral scanner;
   identifying an initial position of the given tooth;
   acquiring an indication of a target position for the given tooth;
   acquiring a stress values range for stress applicable to the given tooth for causing the given tooth to move from the initial position to the target position, the stress value range having been predetermined using a Stress Distribution Cumulative function, the stress values range including:
   a minimum stress value being indicative of a minimum amount of stress for causing the given tooth to move;
   a maximum stress value being indicative of a minimum amount of stress causing permanent damage to the given tooth;
   generating, based on the 3D model of the given tooth, a plurality of segments defining the tooth trajectory of the given tooth from the initial position to the target position, a given segment of the plurality of segments being associated with a start position and with an end position, the given segment of the plurality of segments having been generated by executing an optimization algorithm, the optimization algorithm comprising a gradient descent algorithm, the executing comprising:
   identifying the start position associated with the given segment;
   determining, based on the stress values range, an initial force to be applied to the given tooth, the initial force causing a first maximum displacement, in a predetermined interval, of the 3D model of the given tooth from the start position associated with the given segment towards the target position associated with the given tooth, thereby identifying the end position associated with the given segment,
   the first maximum displacement of the 3D model of the given tooth causing application of a respective force to at least one other of the 3D models of the plurality of subject's teeth, and
   the respective force being determined based on the initial force such that the respective force corresponds to a respective stress values range having been predetermined for a respective one of the plurality of subject's teeth associated with the at least one other of the 3D models; and
   storing data of the given segment of the tooth trajectory of the given tooth including data of the initial force to be applied thereon and the respective force applied to the at least one other of the 3D models of the plurality of subject's teeth for use in planning the orthodontic treatment of the subject.

2. The method of claim 1, wherein:
   applying the initial force to the 3D model of the given tooth causes respective collisions among at least some other of the 3D models of the plurality of subject's teeth including the 3D model of the given tooth; and the method further comprises:
   in response to determining an occurrence of at least one of the respective collisions, iteratively optimizing the initial force until a second maximum displacement of the 3D model of the given tooth is caused, by an optimized initial force, in the predetermined interval, from the start position associated with the given segment towards the target position associated with the given tooth provided that an extent of the at least one of the respective collisions is minimized; and
   wherein:
   the end position associated with the given segment is identified by applying the optimized initial force to the 3D model thereof; and
   the application of the respective force to the at least one other of the 3D models of the plurality of the subject's teeth is caused by the second maximum displacement of the 3D model of the given tooth.

3. The method of claim 2, wherein an extent of a given collision is indicative of a degree of an overlap region between a pair of 3D models of adjacent teeth of the at least some other of the 3D models of the plurality of subject's teeth including the 3D model of the given tooth.

4. The method of claim 2, wherein each occurrence of collision is determined by a collision detection algorithm.

5. The method of claim 1, wherein the respective force is determined based on the initial force using a Displacement Response Distribution function.

6. The method of claim 1, wherein the given segment defines a movement path for the given tooth during the predetermined interval of the orthodontic treatment, and wherein each one of the plurality of segments of the tooth trajectory defines a respective movement path for the given tooth during a respective one of a plurality of predetermined intervals forming a total duration of the orthodontic treatment.

7. The method of claim 6, wherein each one of the plurality of predetermined intervals is equal.

8. The method of claim 7, further comprising generating, by the optimization algorithm, respective tooth trajectories for other ones of the plurality of subject's teeth, and wherein the orthodontic treatment is representable by a schedule defining movements of each one of the plurality of subject's teeth during respective ones of the plurality of predetermined intervals.

9. The method of claim 8, wherein the orthodontic treatment includes applying a respective aligner during each one of the plurality of predetermined intervals.

10. The method of claim 9, further comprising:
in response to modifying the tooth trajectory associated with the given tooth, thereby determining a new tooth trajectory therefor,
the modifying causing respective collisions between at least some other of the 3D models of the plurality of subject's teeth including the 3D model of the given tooth,
re-generating, by the optimization algorithm, based on the new tooth trajectory for the given tooth, trajectories respectively associated with the at least some other of the plurality of subject's teeth.

11. The method of claim 1, wherein the optimization algorithm is configured to generate the given segment to be a line segment.

12. A system for determining a tooth trajectory for a given tooth of a subject, the tooth trajectory defining movements of the given tooth during an orthodontic treatment, the system comprising a processor of an electronic device configured to execute a method, the method comprising:
acquiring a 3D model of an arch form associated with the subject, the 3D model of the arch form including 3D models of a plurality of subject's teeth including a 3D model of the given tooth, the 3D model being based on image data acquired by an intraoral scanner;
identifying an initial position of the given tooth;
acquiring an indication of a target position for the given tooth;
acquiring a stress values range for stress applicable to the given tooth for causing the given tooth to move from the initial position to the target position, the stress value range having been predetermined using a Stress Distribution Cumulative function, the stress values range including:
a minimum stress value being indicative of a minimum amount of stress for causing the given tooth to move;
a maximum stress value being indicative of a minimum amount of stress causing permanent damage to the given tooth;
generating, based on the 3D model of the given tooth, a plurality of segments defining the tooth trajectory of the given tooth from the initial position to the target position, a given segment of the plurality of segments being associated with a start position and with an end position, the given segment of the plurality of segments having been generated by executing an optimization algorithm, the optimization algorithm comprising a gradient descent algorithm, the executing comprising:
identifying the start position associated with the given segment;
determining, based on the stress values range, an initial force to be applied to the given tooth, the initial force causing a first maximum displacement, in a predetermined interval, of the 3D model of the given tooth from the start position associated with the given segment towards the target position associated with the given tooth, thereby identifying the end position associated with the given segment,
the first maximum displacement of the 3D model of the given tooth causing application of a respective force to at least one other of the 3D models of the plurality of subject's teeth, and
the respective force being determined based on the initial force such that the respective force corresponds to a respective stress values range having been predetermined for a respective one of the plurality of subject's teeth associated with the at least one other of the 3D models;
and
storing data of the given segment of the tooth trajectory of the given tooth including data of the initial force to be applied thereon and the respective force applied to the at least one other of the 3D models of the plurality of subject's teeth for use in planning the orthodontic treatment of the subject.

13. The system of claim 12, wherein:
applying the initial force to the 3D model of the given tooth causes respective collisions among at least some other of the 3D models of the plurality of subject's teeth including the 3D model of the given tooth; and the method further comprises:
in response to determining an occurrence of at least one of the respective collisions, iteratively optimizing the initial force until a second maximum displacement of the 3D model of the given tooth is caused, by an optimized initial force, in the predetermined interval, from the start position associated with the given segment towards the target position associated with the given tooth provided that an extent of the at least one of the respective collisions is minimized; and wherein:
the end position associated with the given segment is identified by applying the optimized initial force to the 3D model thereof; and
the application of the respective force to the at least one other of the 3D models of the plurality of the subject's teeth is caused by the second maximum displacement of the 3D model of the given tooth.

14. The system of claim 13, wherein an extent of a given collision is indicative of a degree of an overlap region between a pair of 3D models of adjacent teeth of the at least some other of the 3D models of the plurality of subject's teeth including the 3D model of the given tooth.

15. The system of claim 14, wherein to determine each occurrence of collision, the processor is configured to apply a collision detection algorithm.

16. The system of claim 12, wherein to determine the respective force based on the initial force, the processor is configured to apply a Displacement Response Distribution function.

17. The system of claim 12, wherein the given segment defines a movement path for the given tooth during the predetermined interval of the orthodontic treatment, and wherein each one of the plurality of segments of the tooth trajectory defines a respective movement path for the given tooth during a respective one of a plurality of predetermined intervals forming a total duration of the orthodontic treatment; and the processor is further configured to:
- generate, by the optimization algorithm, respective tooth trajectories for other ones of the plurality of subject's teeth, and wherein the orthodontic treatment is representable by a schedule defining movements of each one of the plurality of subject's teeth during respective ones of the plurality of predetermined intervals;
- in response to modifying the tooth trajectory associated with the given tooth, thereby determining a new tooth trajectory therefor,
    - the modifying causing respective collisions between at least some other of the 3D models of the plurality of subject's teeth including the 3D model of the given tooth;
- re-generate, by the optimization algorithm, based on the new tooth trajectory for the given tooth, trajectories respectively associated with the at least some other of the plurality of subject's teeth.

* * * * *